(12) United States Patent
Roewer et al.

(10) Patent No.: US 9,949,947 B2
(45) Date of Patent: *Apr. 24, 2018

(54) DELPHINIDIN FOR COMBATING MELANOMA CELLS

(71) Applicant: Sapiotec GmbH, Wurzburg (DE)

(72) Inventors: Norbert Roewer, Wurzburg (DE); Jens Broscheit, Wurzburg (DE)

(73) Assignee: SAPIOTEC GMBH, Wurzburg (DE)

( * ) Notice: Subject to any disclaimer, the term of this patent is extended or adjusted under 35 U.S.C. 154(b) by 97 days.

This patent is subject to a terminal disclaimer.

(21) Appl. No.: 14/651,262

(22) PCT Filed: Nov. 28, 2013

(86) PCT No.: PCT/EP2013/074957
§ 371 (c)(1),
(2) Date: Jun. 11, 2015

(87) PCT Pub. No.: WO2014/090583
PCT Pub. Date: Jun. 19, 2014

(65) Prior Publication Data
US 2015/0328336 A1 Nov. 19, 2015

(30) Foreign Application Priority Data

Dec. 11, 2012 (DE) .................. 10 2012 222 777
Jan. 11, 2013 (EP) ...................... 13150909

(51) Int. Cl.
| | |
|---|---|
| A61K 31/7048 | (2006.01) |
| A61K 47/40 | (2006.01) |
| A61K 31/352 | (2006.01) |
| A61K 38/19 | (2006.01) |
| A61K 45/06 | (2006.01) |
| A61K 38/17 | (2006.01) |
| A61K 31/7042 | (2006.01) |
| A61K 47/48 | (2006.01) |
| B82Y 5/00 | (2011.01) |

(52) U.S. Cl.
CPC ........ *A61K 31/352* (2013.01); *A61K 31/7042* (2013.01); *A61K 38/1793* (2013.01); *A61K 38/191* (2013.01); *A61K 45/06* (2013.01); *A61K 47/48969* (2013.01); *B82Y 5/00* (2013.01)

(58) Field of Classification Search
None
See application file for complete search history.

(56) References Cited

U.S. PATENT DOCUMENTS

| | | | |
|---|---|---|---|
| 4,826,963 A | 5/1989 | Stadler nee Szoke et al. | |
| 5,134,127 A | 7/1992 | Stella et al. | |
| 6,576,261 B1 | 6/2003 | Pitha | |
| 6,699,849 B1 | 3/2004 | Loftsson et al. | |
| 7,034,013 B2 | 4/2006 | Thompson et al. | |
| 8,980,882 B2 | 3/2015 | Roewer et al. | |
| 9,006,215 B2 | 4/2015 | Roewer et al. | |
| 9,125,953 B2 | 9/2015 | Roewer et al. | |
| 2004/0101933 A1 | 5/2004 | Matsumoto et al. | |
| 2005/0013880 A1 | 1/2005 | Magnuson et al. | |
| 2005/0164986 A1 | 7/2005 | Mosher | |
| 2005/0239746 A1 | 10/2005 | Penkler et al. | |
| 2007/0093448 A1 | 4/2007 | Westermann et al. | |
| 2007/0232688 A1 | 10/2007 | Orchansky et al. | |
| 2009/0270348 A1 | 10/2009 | Antle | |
| 2011/0015145 A1 | 1/2011 | Bodor | |
| 2011/0028386 A1 | 2/2011 | Hodges et al. | |
| 2011/0224168 A1 | 9/2011 | Szente | |
| 2012/0083460 A1 | 4/2012 | Emura et al. | |
| 2015/0051273 A1 | 2/2015 | Roewer et al. | |
| 2015/0087822 A1 | 3/2015 | Roewer et al. | |
| 2015/0258202 A1 | 9/2015 | Roewer et al. | |
| 2015/0306247 A1 | 10/2015 | Roewer et al. | |
| 2015/0320719 A1 | 11/2015 | Roewer et al. | |

FOREIGN PATENT DOCUMENTS

| | | | |
|---|---|---|---|
| CN | 1672534 | 9/2005 | |
| CN | 1696304 | 11/2005 | |
| DE | 102010042615 | 4/2012 | |
| EP | 0214647 | 3/1987 | |
| EP | 0390496 | 10/1990 | |
| EP | 1704858 | 9/2006 | |
| GB | 2350297 | 11/2000 | |
| JP | 59-46228 | 3/1984 | |
| JP | 2003-171274 | 6/2003 | |
| JP | 2003-522207 | 7/2003 | |
| JP | 2004-526730 | 9/2004 | |
| JP | 2005-522422 | 7/2005 | |
| JP | 2009-167174 | 7/2009 | |
| KR | 10-2007-0026284 | 3/2007 | |
| KR | 10-2007-0028640 | * 3/2007 | ........... A61K 31/352 |
| WO | WO 1996/32135 | 10/1996 | |
| WO | WO 1997/17977 | 5/1997 | |

(Continued)

OTHER PUBLICATIONS

U.S. Appl. No. 14/443,166, filed May 2015, Roewer.*
U.S. Appl. No. 14/389,474, filed Sep. 2014, Roewer.*
U.S. Appl. No. 14/432,654, filed Mar. 2015, Roewer.*
Kanakis et al., DNA Interaction with Naturally Occurring Antioxidant Flavonoids Quercetin, Kaempferol, and Delphinidin, pp. 719-724, published online: May 15, 2012.*
Kumoro et al, Solubility of Delphinidin in Water and Various Organic Solvents between (298.15 and 343.15) K; 2012; J. Chem. Eng. Data; 55: 2603-2606.*

(Continued)

*Primary Examiner* — Svetlana M Ivanova

(74) *Attorney, Agent, or Firm* — Casimir Jones, S.C.; Mary Ann Brow

(57) ABSTRACT

The invention relates to a composition comprising a complex of delphinidin and a sulfoalkyl ether-β-cyclodextrin for use in the treatment of malignant melanoma.

19 Claims, 21 Drawing Sheets

(56) References Cited

FOREIGN PATENT DOCUMENTS

| | | |
|---|---|---|
| WO | WO 1999/24073 | 5/1999 |
| WO | WO 1999/42211 | 8/1999 |
| WO | WO 2001/030391 | 5/2001 |
| WO | WO 2002/074200 | 9/2002 |
| WO | WO 2003/063824 | 8/2003 |
| WO | WO 2003/080079 | 10/2003 |
| WO | 2006076387 | 7/2006 |
| WO | WO 2008/070490 | 6/2008 |
| WO | WO 2008/126979 | 10/2008 |
| WO | WO 2009/018326 | 2/2009 |
| WO | WO 2009018326 A2 * 2/2009 ........... A61K 31/352 |
| WO | WO 2009/134347 | 11/2009 |
| WO | WO 2011/048479 | 4/2011 |
| WO | WO 2011/086146 | 7/2011 |
| WO | WO 2012/090018 | 7/2012 |
| WO | WO 2013/144297 | 10/2013 |
| WO | WO 2013/144303 | 10/2013 |
| WO | WO 2013/144306 | 10/2013 |
| WO | WO 2014/060548 | 4/2014 |
| WO | WO 2014/075935 | 5/2014 |
| WO | WO 2014/090583 | 5/2014 |
| WO | WO 2014/090586 | 6/2014 |
| WO | WO 2015/128419 | 9/2015 |
| WO | WO 2015/128437 | 9/2015 |

OTHER PUBLICATIONS

Biolink, Biolink synthetic anthocyanin molecules becomes cancer fighters, dated May 22, 2009, http://www.biolink.no/biolink/cancer-article95-6.html, retrieved Feb. 21, 2013, 4 pages.*

Voersmann et. al., J. Invest. Dermatol. (2012) S129, Abstract #737.*

Pehamberger, Adjuvant interferon alfa-2a treatment in resected primary stage II cutaneous melanoma. Austrian Malignant Melanoma Cooperative Group, Journal of Clinical Oncology, vol. 16, No. 4 (April), 1998: pp. 1425-1429.*

Afaq et al., Delphinidin, an anthocyanidin in pigmented fruits and vegetables, protects human HaCaT keratinocytes and mouse skin against UVB-mediated oxidative stress and apoptosis, J Invest Dermatol. Jan. 2007;127(1):222-32.

Biolink synthetic anthocyanin molecules becomes cancer fighters, www.biolink.no/biolink/cancer-articles95-6.html, May 22, 2009, 4 pages.

Serafino et al., Differentiation of human melanoma cells induced by cyanidin-3-O-beta-glucopyranoside, FASEB J. Dec. 2004;18(15):1940-2.

Ueda et al., Evaluation of a sulfobutyl ether beta-cyclodextrin as a solubilizing/stabilizing agent for several drugs, Drug Dev Ind Pharm. Sep. 1998;24(9):863-7.

Wang et al., Anthocyanins and their role in cancer prevention, Cancer Lett. Oct. 8, 2008;269(2):281-90.

Abdollahzadeh et al., Antibacterial and Antifungal Activities of Punica Granatum Peel Extracts Against Oral Pathogens. Journal of Dentistry, Tehran University of Medical Sciences 2011; 8: 1-6.

Armstrong et al., Separation of drug stereoisomers by the formation of beta-cyclodextrin inclusion complexes. Science. May 30, 1986;232(4754):1132-5.

ATCC product sheet for A-375 [A375] (ATCC CRL-1619), retrieved Nov. 16, 2015, 3 pages.

Bertuglia et al., Microvascular Effects of a Natural Flavonoid (IdB 1056) During Ischemia-Reperfusion Injury, Pharmacological Research 1990; 22:52, Abstract.

Biofiles: Nutrition Research. Sigma-Aldrich. 2007;2:1-28.

Braga et al., Inclusion of molybdenocene dichloride (Cp2MoCl2) in 2-hydroxypropyl- and trimethyl-beta-cyclodextrin: Structural and biological properties. Journal of Organometallic Chemistry, 2005; 690:2905-2912.

Brewster et al., Cyclodextrins as pharmaceutical solubilizers. Adv Drug Deliv Rev. Jul. 30, 2007;59(7):645-66.

Bruggen, Detection of phenotypic differences on human malignant melanoma lines and their variant sublines with monoclonal antibodies, Cancer Immunol Immunother, 1983, 15:200-205.

Burdulis et al., "Comparative Study of Anthocyanin Composition, Antimicrobial and Antioxidant Activity in Bilberry (*Vaccinium myrtillus* L.) and Blueberry (*Vaccinium corymbosum* L.) Fruits." Acta Poloniae Pharmaceutica 2009; 66:399-408.

Cyclobond Handbook, A Guide to Using Cyclodextrin Bonded Phases for Chiral LC Seperations, 6th ed., 2002, Advanced Seperation Technologies, Inc., pp. 1-58.

Eftink et al., Calorimetric studies of p-nitrophenol binding to alpha- and beta-cyclodextrin. Bioorganic Chemistry. 1981;10:388-398.

Hornle et al., Caspase-3 cleaves XIAP in a positive feedback loop to sensitize melanoma cells to TRAIL-induced apoptosis. Oncogene. Feb. 3, 2011;30(5):575-87.

Hutajalu et al., "Identification of Phenol and Delphinidine in the Telangs flower (*Clitoria ternatea* L.) and Its Effectivity to *Staphylococcus aureus* as Eyes Bacteria Disease." Journal of Agro-Based Industry 2008; 25: 35-44.

Ibrahium, Efficiency of Pomegranate Peel Extract as Antimicrobial, Antioxidant and Protective Agents. World Journal of Agricultural Sciences 2010; 6: 338-344.

Immel, Ph.D. Thesis, Darmstadt University of Technology, 1995. Computer Simulation of Chemical and Biological Properties of Saccharides: Sucrose, Fructose, Cyclodextrins, and Starch; Chapter 7. "Some Reflections on the Multitude of Cyclodextrin Isomers: Astronomic Numbers as a Justification for Computational Studies prior to Synthesis", 9 pages.

Jara et al., The interaction of solvtochromic pyridiniophenolates with cyclodextrins. Tetrahedron. 2006;62:7817-7823.

Kamei et al., "Suppression of tumor cell growth by anthocyanins in vitro." Cancer Invest 1995; 13: 590-594.

Kumoro et al., Solubility of Delphinidin in Water and Various Organic Solvents between (298.15 and 343.15)K. J Chem Eng Data. 2012;55:2603-2606.

Lecis et al., Novel SMAC-mimetics synergistically stimulate melanoma cell death in combination with TRAIL and Bortezomib. Br J Cancer. Jun. 8, 2010;102(12):1707-16.

Naber, *Staphylococcus aureus* Bacteremia: Epidemiology, Pathophysiology, and Management Strategies. Clin Infect Dis. 2009;48(Suppl 4):S231-S237.

Riccardi et al., Analysis of apoptosis by propidium iodide staining and flow cytometry. Nat. Protoc., 2006, 1:1458-1461.

Scarabelli et al., Targeting STAT1 by myricetin and delphinidin provides efficient protection of the heart from ischemia/reperfusion-induced injury, FEBS Lett. Feb. 4, 2009;583(3):531-41.

Stella et al., Cyclodextrins: their future in drug formulation and delivery. Pharm Res. May 1997;14(5):556-67.

Ukoka et al., Tannins and other phytochemical of the Samanaea saman pods and their antimicrobial activities, African Journal of Pure and Applied Chemistry 2011; 5: 237-244.

Vierstein et al., Intravenous anasthesia with isoflurane in the rabbit. Pharm Pharmacol Lett, 1994; 3:165-168.

Vierstein et al., Preparation and central action of propofol/hydroxypropyl-beta-cyclodextrin complexes in rabbits. Arzneimittelforschung. Aug. 1993;43(8):818-21.

English translation of IPRP for International Patent Application PCT/EP2011/050428, dated Aug. 16, 2012, 8 pages.

International Search Report for PCT/EP2013/056707, dated Mar. 28, 2013, 13 pages. With Translation.

International Search Report for PCT/EP2013/056725 dated Apr. 7, 2013, 17 pages. With Translation.

International Search Report for PCT/EP2013/071779 dated Dec. 10, 2013, 12 pages. With Translation.

International Search Report for PCT/EP2015/054023 dated Mar. 23, 2015, 10 pages. With Translation.

International Search Report for PCT/EP2015/054084 dated May 4, 2015, 17 pages. With Translation.

* cited by examiner

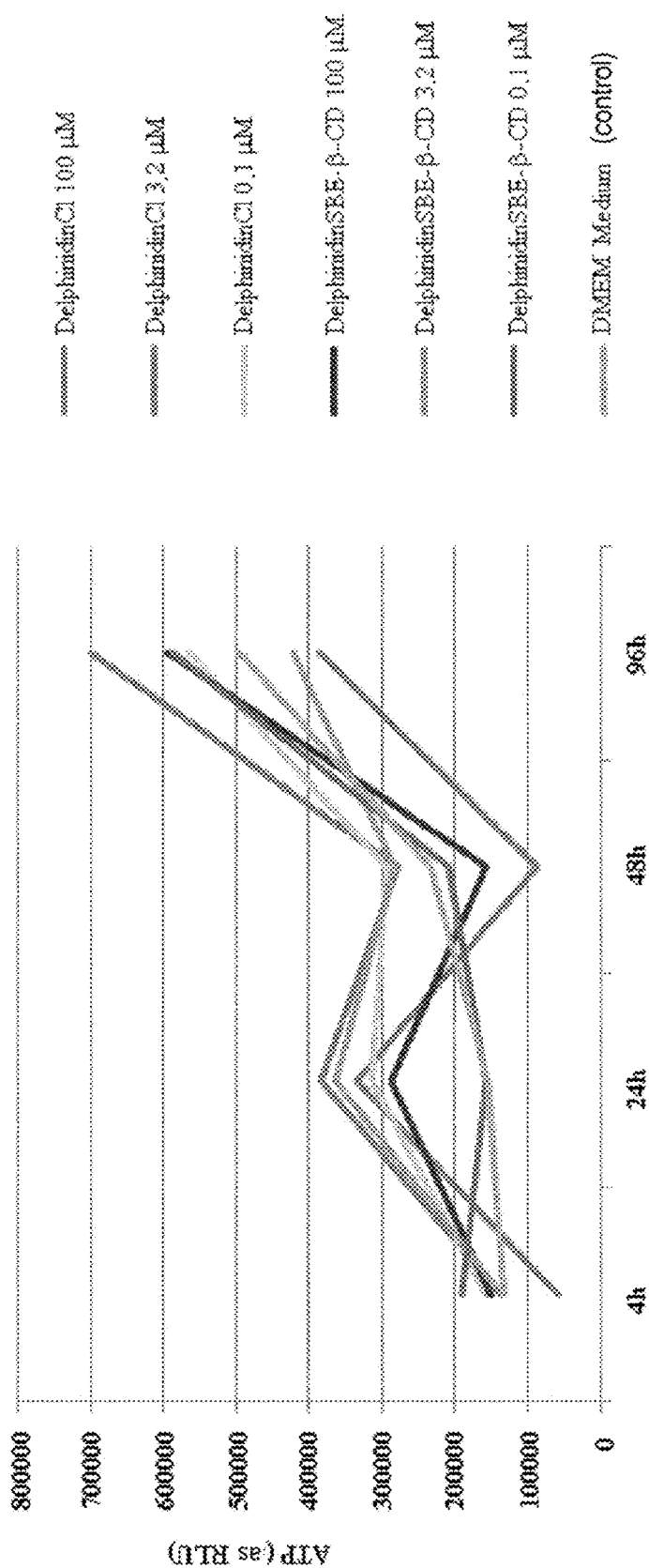

DELPHINIDIN FOR COMBATING MELANOMA CELLS

This application is a § 371 US National Entry of International Application No. PCT/EP2013/074957, filed Nov. 28, 2013, which claims the benefit of European Application No. 13150909.3, filed Jan. 11, 2013 and German Application No. 102012222777.6, filed Dec. 11, 2012.

The invention relates to compositions comprising
a complex of delphinidin and a sulfoalkyl ether β-cyclodextrin and/or
delphinidin or salts thereof
for use in the treatment of malignant melanoma.

Malignant melanoma, also known by the term "black skin cancer", is a malignant degeneration of pigment cells, the so-called melanocytes. Cancer has a tendency even in an early stage to spread metastases via the circulatory and lymphatic systems. Malignant melanoma is curable, at least if it is diagnosed and treated early.

The most important treatment method is the surgical removal of the tumor in addition to radiotherapy, although monotherapy with interferons is also used in the treatment of malignant melanoma. Vaccine therapy is also known, i.e. active immunotherapy by means of tumor inoculation using tumor vaccines in order to stimulate the body's own resistance for specific combating of cancer cells. In this case, features of the tumor (for example, protein molecules produced by the tumor cells or cell fragments of the tumor cells) are presented to the immune cells via the vaccines administered such that the immune cells recognize these features as foreign and attack the body's own cells, which bear these features. In addition to vaccine therapy, chemotherapy, i.e. medical treatment with chemical substances that damage or inhibit tumor cells (cytostatics), is of practical relevance.

The object of the present invention is to provide an effective remedy as an alternative or supplement to the treatment options for malignant melanoma known from the prior art.

This object is achieved by the compositions and uses cited in the independent claims, whereas advantageous embodiments of the invention are disclosed in the dependent claims. That this object is, in fact, achieved, is proven by the in vitro experimental results of the effect of the compositions according to the invention on melanoma cells and non-cancerous cells and the cell vitality in Examples 6-12.

Firstly, some terms used in the context of the invention are elucidated.

The composition according to the invention is used for treating a subject or an individual suffering from malignant melanoma. The term "subject" comprises living animals and humans. The purpose of this treatment is the at least partial killing or neutralization of the tumor cells. "Neutralization" or "killing" signifies, in the context of the present invention, the at least partial destruction or disintegration or inactivation or proliferation of tumor cells.

The present invention also refers to a method for treating a subject suffering from malignant melanoma, in which a therapeutically active amount of the composition according to the invention is administered to the subject. Of particular interest here is combating the melanoma cells with the active ingredient on the one hand while as far as possible leaving unaffected the vitality and proliferation of the non-cancerous cells on the other hand.

The term "treatment" signifies, in the context of the present invention, complete or partial achievement of the following specified results: completely or partially reducing the clinical picture; improving at least one of the clinical symptoms or indicators associated with the disease; delaying, suppressing or providing protection from the progression of the disease; or completely or partially delaying, suppressing or providing protection from onset or development of the disease. The subject to be treated is a human or animal, preferably a mammal. Veterinary medical treatment, besides the treatment of livestock or wild animals (e.g. sheep, cats, horses, cows, pigs), also includes laboratory animals (e.g. rats, mice, guinea pigs, monkeys).

The term "composition comprising a complex of delphinidin and a sulfoalkyl ether β-cyclodextrin and/or delphinidin or salts thereof" includes the composition as a monopreparation, i.e. without further therapeutically active components. Alternatively, the composition may comprise at least one further therapeutically active substance. The composition according to the invention can be administered alone or in combination with at least one other therapeutic substance for reducing one or more symptoms of malignant melanoma. The administration of the composition according to the invention can be administered simultaneously with the other therapeutic substance, which can be a constituent of the same composition or is provided in another composition. Alternatively, the composition according to the invention can be administered before or after the administration of the other therapeutic substance. The composition according to the invention can be administered via the same route of administration as or a different route of administration to the other therapeutic substance.

The further therapeutically active substance is preferably a Tumor necrosis factor-Related Apoptosis-Inducing Ligand (TRAIL). In accordance with a further preferred embodiment of the invention, the further therapeutically active substance is selected from the group consisting of cytostatics, interferons, preferably alpha- and/or beta-interferons, more preferably interferon alpha-2a and alpha-2b, and tumor vaccines. The latter can also be combined and applied in combination with TRAIL.

Particularly if metastases have already formed in other organs, a combination of chemotherapy and immunotherapy, and radiation treatment of individual metastases may be appropriate in order to achieve regressions.

Interferons are typically used in chemotherapy, particularly IFN-alpha formed in white blood cells (leucocytes) and IFN-beta formed in connective tissue cells (fibroblasts), which inhibit the growth of healthy as well as malignant cells and stimulate the immune system. A pure interferon obtained by gene technology is usually relied on in cancer therapy, for example, interferon alpha-2a (Roferon®) and interferon alpha-2b (IntronA®) approved for cancer treatment in Germany.

From immunotherapy comes the original concept, which is increasingly rarely used, in which the body's own tumor cells are rendered incapable of dividing by irradiation and, to increase stimulation of the immune system, are injected into the skin, preferably mixed with a virus, in order to attract immune cells and to selectively target these tumor cells. Instead of using whole tumor cells or cell fragments, protein molecules produced by tumor cells, with which cells cultured from blood precursor cells in vitro are charged, are now regularly relied upon and, thus tailored, are given back to the patient to present them to immune cells as something which must be combated. Alternatively, the same result is achieved if the gene for an attractant or activating substance for immune cells is inserted into the tumor cells.

Also of practical relevance is the abovementioned chemotherapy directed against cancer cells in which various medicaments are used which can inhibit tumor growth in a different way, these chemotherapeutics usually being referred to as "cytostatics". Cytostatics are prepared synthetically or are derived from naturally-occurring cytotoxins which trigger the programmed cell death (apoptosis) of the tumor cells. Examples of chemotherapeutic agents which may be used in the context of the present invention include bortezomib (Velcade®, Millennium), melphalan, prednisone, vincristine, carmustine, cyclophosphamide, dexamethasone, thalidomide, doxorubicin, cisplatin, etoposide and cytarabine.

In addition to the drug administration according to the invention, radiotherapy can additionally be used. Apart from the use of radioactive drugs, so-called "radiopharmaceuticals", radiotherapy is preferably used locally in a limited manner. This means that the preferably electromagnetic radiation and particle beams as well act locally in this case limited to the irradiated area and damage the tumor cells, particularly the DNA in the cell nucleus, by ionization and formation of free radicals and breaks in the DNA of the tumor cells. In order to protect the healthy tissue surrounding the tumor, screens can be used.

The administration of the active ingredient of the invention by way of monotherapy or in combination with TRAIL or other or further therapeutic active ingredients, for example selected from the group consisting of cytostatics, interferons and tumor vaccines, can also be done as a so-called regional therapy, for example by targeted injection (e.g. by means of a catheter) in body regions, body cavities or into the blood vessels of the tumor region or organ in which the tumor is located. Permeation of the affected area or organ is also possible by means of regional perfusion, in which the medicament flows through the area (e.g. arm or leg) or the organ on completion of the remaining circulation and is passed directly through again without reaching the rest of the body.

The composition according to the invention is preferably provided and administered as a pharmaceutical composition. The term "pharmaceutical composition" comprises one or more active ingredients and one or more inactive ingredients which function as carriers for the active ingredient(s). The pharmaceutical composition allows the complex according to the invention or the composition according to the invention to be administered by the oral, rectal, parenteral, including intraperitoneal, percutaneous, subcutaneous, intramuscular, intravenous, ophthalmic, pulmonary or nasal routes. A parenteral administration form may be, for example, a tablet, capsule, solution, suspension or dispersion. An ophthalmic, pulmonary or nasal administration form may be, for example, an aerosol, solution, cream, paste, lotion, gel, salve, suspension or dispersion. Appropriate techniques for formulation and administration are known from the prior art, for example, see "Remington's Pharmaceutical Sciences" (Mack Publishing Co., Easton Pa.). For example, the compositions according to the invention can be administered intravenously to a subject by means of a pharmaceutically acceptable carrier (e.g. physiological saline solution). A formulation in aqueous solution, preferably in physiologically acceptable buffers (e.g. Hank's solution, Ringer's solution or physiologically buffered saline solution), is suitable for injection. For parenteral administration, including intravenous, subcutaneous, intramuscular and intraperitoneal administration, an aqueous or oily solution or a solid formulation is also useful. The proportion of active ingredient in the pharmaceutical composition may vary and is typically between 2 and 60% by weight of the dose unit. The proportion of active ingredient is accordingly selected such that an effective dose is achieved. In accordance with a preferred embodiment of the invention, the delphinidin or salts thereof and/or the complex of delphinidin and the sulfoalkyl ether β-cyclodextrin are used in a galenic preparation for controlled and/or delayed release of the delphinidin.

"Salt" or "pharmaceutically acceptable salt" is any salt of a compound of the present invention, acceptable from a pharmaceutical standpoint, which can liberate the pharmaceutically effective active ingredient or active metabolite thereof after administration. Salts of the compositions and complexes of the present invention may be derived from inorganic or organic acids and bases.

The anthocyanidin delphinidin may be used in "pure form" or "purified", which signifies that undesired components have been removed.

"Anthocyanidins" have the basic structure shown below:

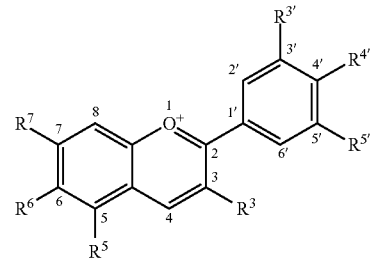

The substituents in this formula are selected from the group consisting of hydrogen, hydroxyl group, and methoxy group.

Cyclodextrins, which can be complexed with the anthocyanidin delphinidin in accordance with the invention, are cyclic oligosaccharides of glucose molecules linked by α-1,4-glycosidic bonds. β-cyclodextrin has seven glucose units. In a sulfoalkyl ether β-cyclodextrin, hydroxyl groups of the glucose unit in a sulfoalkyl alcohol are etherified. According to the invention, generally only some of the 21 hydroxyl groups of a β-cyclodextrin are etherified. The preparation of sulfoalkyl ether cyclodextrins is familiar to those skilled in the art and is described, for example, in U.S. Pat. No. 5,134,127 or WO 2009/134347 A2.

Sulfoalkyl ether groups are used in cyclodextrins in the prior art to increase their hydrophilicity or water solubility. Sulfoalkyl ether groups contribute to a particular degree to increasing the stability of the complex of anthocyanidins and correspondingly substituted β-cyclodextrin and thus substantially improve the storage stability and formulatability of the anthocyanidins, which are particularly sensitive to oxidation. The complex according to the invention may be formulated as an aqueous solution or solid, stable on storage, as will be shown in even more detail below.

In accordance with the invention, particular preference is given to complexing the active ingredient delphinidin with a sulfoalkyl ether β-cyclodextrin, preferably a sulfobutyl ether β-cyclodextrin (SBE-β-CD) or a sulfoethyl ether β-cyclodextrin, which increases, surprisingly, the solubility and stability of the active ingredient. A possible explanation for this, which does not limit the scope of protection, is that the negatively charged sulfobutyl units or sulfoethyl units interact electrostatically with the positively charged anthocyanidin delphinidin and, in terms of the alkyl groups, the butyl group or ethyl group have the optimal length to enable an appropriate steric interaction. It should be noted at this point, that no generally valid statement can be made that any active ingredient, such as delphinidin, in a complex with a sulfoalkyl ether β-cyclodextrin, results in improved solubility and stability. Reference may be made at this point, for example, to Table 1 in Ueda et al., "Evaluation of a Sulfobutyl Ether β-Cyclodextrin as a Solubilizing/Stabilizing Agent for Several Drugs", Drug Development and Industrial Pharmacy, 24 (9), 863-867 (1998), in which the solubilities of various active ingredients alone, in the complex with sulfobutyl ether β-cyclodextrin and in the complex with β-cyclodextrin, are contrasted. From the solubility values (SBE7-β-CD vs. β-CD) shown therein, it can be seen that in one third of the active ingredients complexed with sulfobutyl ether β-cyclodextrin investigated, the exact opposite is the case, i.e. the complex of active ingredient and sulfobutyl ether β-cyclodextrin results in a significantly lower solubility compared to the complex with β-cyclodextrin.

The degree of substitution of the cyclodextrin with sulfoalkyl ether groups is preferably 3 to 8, more preferably 4 to 8, more preferably 5 to 8, more preferably 6 to 7. Suitable sulfobutyl ether β-cyclodextrins having a mean degree of substitution of 6 to 7 are described, for example, in WO 2009/134347 A2 and are commercially available under the trade name Captisol®. Corresponding cyclodextrins having a degree of substitution of 4 to 5, for example 4.2, can likewise be used.

The anthocyanidin used in complexed form in accordance with the invention is delphinidin. The chemical structure corresponds to the formula given above with the following substitution pattern

|  | $R^{3'}$ | $R^{4'}$ | $R^{5'}$ | $R^3$ | $R^5$ | $R^6$ | $R^7$ |
|---|---|---|---|---|---|---|---|
| Delphinidin | —OH | —OH | —OH | —OH | —OH | —H | —OH |

The invention also relates to an aqueous solution of the composition according to the invention for use as a medicament for the treatment of malignant melanoma.

The preparation of the complex according to the invention, and also a corresponding aqueous solution comprises the following steps:
a) preparing an aqueous solution of the sulfoalkyl ether β-cyclodextrin,
b) adding the anthocyanidin delphinidin and mixing to prepare the complex.

In step a), preference is given to preparing an aqueous solution comprising 5 to 10% by weight of the cyclodextrin used. It is particularly preferred in the context of the invention if the pH of the aqueous solution is adjusted during or after, but preferably before, addition of the delphinidin, to a pH of 7 or less, preferably 6 or less, more preferably 5 or less, more preferably 4 to 5. It has been shown that, at this pH, a higher concentration of the complex in aqueous solution can be established.

The concentration of the delphinidin, calculated as the chloride, is preferably at least 0.5 mg/ml, more preferably at least 1.0 mg/ml, more preferably at least 1.5 mg/ml, more preferably 2.0 mg/ml. In the context of a preferred embodiment, the particularly preferred concentration range of at least 2.0 mg/ml can be established in particular in an aqueous solution having a pH between 4 and 5.

In the context of the preparation, the mixing of the constituents of the aqueous solution can be accomplished by stirring with preferred periods for the mixing of 2 to 20 h. The mixing is preferably carried out in the dark in order to avoid light-induced oxidation.

The invention further relates to a solid for use as a medicament in the treatment of malignant melanoma, which can be obtained in accordance with the invention by removing the solvent from an aqueous solution according to the invention described above. The removal can preferably be effected by freeze drying (lyophilization). Both the aqueous medicinal solution according to the invention and the medicinal solid have good storage stability.

The invention will now be described further in the examples which follow with reference to the attached figures without being restricted to them.

FIG. 19 shows the effect of delphinidin Cl and the delphinidin-SBE-β-CD complex at concentrations of 0.1 µM, 3.2 µM and 100 µM compared to active ingredient-free control medium on the vitality of human fibroblasts using the ATP luminescence assay.

EXAMPLES

Figure 1:
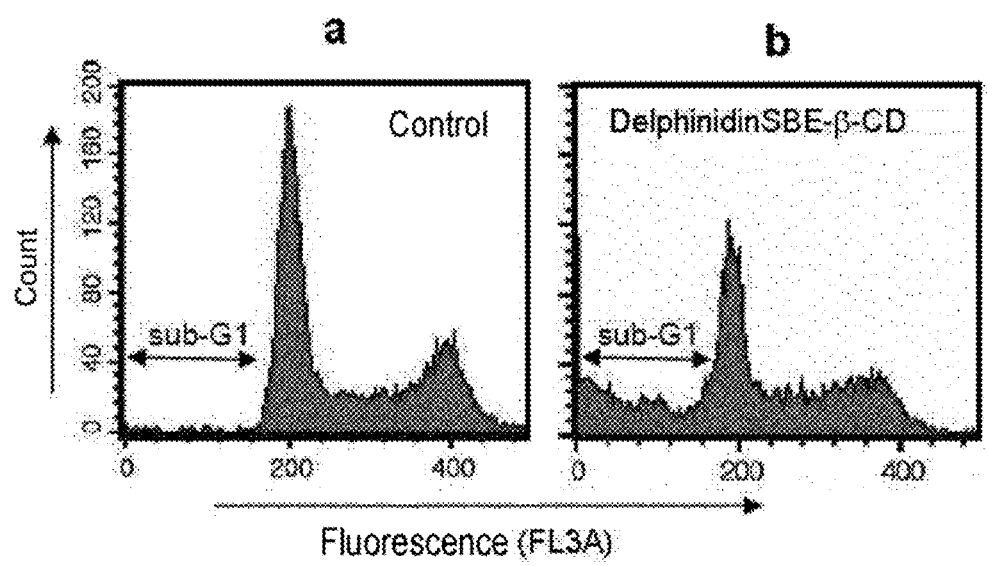
FIG. 1 shows histograms of cells of the human melanoma cell line A-375 treated with delphinidin-SBE-β-CD (b) and untreated (a).

I. Preparation of a Complex of Delphinidin and Cyclodextrins

1. Materials Used:
The following cyclodextrins are used:

| α-CD | ID No: CYL-2322 |
| β-CD | ID No: CYL-3190 |
| γ-CD | ID No: CYL-2323 |
| (2-Hydroxypropyl)-β-CD | ID No: L-043/07 |
| Sulfobutyl ether β-CD | ID No: 47K010111 |

Delphinidin chloride was purchased from Extrasynthese.

2. Determination of the Delphinidin Content

A reversed-phase HPLC method was used to determine the delphinidin chloride content in the delphinidin-containing compositions. The following reagents were used for this purpose:
Purified water
Methanol for chromatography
Formic acid, p.a.
1 M hydrochloric acid as a volumetric solution.

The column used was a Waters×Bridge™ C18, 35 µl, 150 mm×4.6 mm.

The mobile phases were as follows:
Phase A: Water 950 ml, methanol 50 ml, formic acid 10 ml
Phase B: Water 50 ml, methanol 950 ml, formic acid 10 ml
The following gradient program was used:

| Time [min] | Percent phase B |
|---|---|
| 0 | 0 |
| 5 | 0 |
| 25 | 60 |
| 30 | 100 |

Stop time: 35 min
After-run time (post time): 8 min
Flow rate: 1 ml/min
Injection volume: 20 µl
Column temperature: 30° C. +/−2° C.
UV/Vis detector: 530 µm for the assay, 275 µm for the detection of impurities
Integrator: area
Solutions and Sample Preparation:
Dilution solution 1: Mixture of 100 ml of methanol and 2.6 ml of M HCl
Dilution solution 2: Mixture of 100 ml of 40% methanol and 2.6 ml of 1 M HCl Calibration solution: A reference solution of delphinidin was prepared by weighing 10 mg of delphinidin chloride into a 10 ml flask and dissolving in dilution solution 1. After dissolution, the solution was diluted approximately 10-fold with dilution solution 2 to produce an approximate concentration of 0.1 mg/ml.

The control calibration solution was prepared in the same manner. The calibration solutions were immediately analyzed by HPLC since delphinidin chloride is unstable in solution.

Preparation of the test solutions:
To determine the delphinidin content of the solids prepared according to the invention (for preparation see below), approximately 50 mg of this composition were weighed into a 10 ml flask. This was then dissolved in dilution solution 2 and further diluted with the same dilution solution 2 until an approximate concentration of delphinidin of 0.1 mg/ml was established.

The determination of the delphinidin content in the samples was calculated with the aid of the Agilent ChemStation software using calibration with the external standard described.

Example 1

Complexing of Delphinidin with SBE-β-CD

In this example, the complexing of delphinidin by various cyclodextrins and the solubility of the complex in aqueous solution are investigated.

Neutral aqueous solutions were prepared comprising 10% by weight of the respective cyclodextrin. Due to the lack of solubility of β-CD, a concentration of only 2% by weight was selected.

Glass flasks were filled with 5 ml each of the aqueous cyclodextrin solutions and pure water. An excess of delphinidin chloride was then added. The required excess amount was 10 mg for the solutions of α-, β- and γ-cyclodextrin and 15 mg for the solutions of HPBCD (2-hydroxypropyl-β-cyclodextrin) and SBE-β-CD.

The suspensions were stirred at 30° C. for 20 h in the dark. The suspensions were then filtered through a membrane filter of 0.22 μm pore size.

The solubilities achievable are shown in the table below.

| Cyclodextrin | Cyclodextrin concentration | Delphinidin chloride |
|---|---|---|
| — | 0 | 0.07 mg/ml |
| α-CD | 10% | 0.14 mg/ml |
| β-CD | 2% | 0.05 mg/ml |
| γ-CD | 10% | 0.21 mg/ml |
| HPBCD | 10% | 0.19 mg/ml |
| SBE-β-CD | 10% | 0.66 mg/ml |

It can be seen that the complexing and the increased solubility thereby effected is far better for SBE-β-CD than for the other cyclodextrins.

Example 2

Influence of pH

In this example, the influence of the pH on the solubility of a delphinidin-SBE-β-CD in aqueous solution was investigated. Aqueous solutions of SEB-β-CD were prepared according to the procedure of Example 1, but these solutions were adjusted with 1 M HCl to the acid pH values given in Table 2. Delphinidin chloride was then added according to the procedure of Example 1 and further processed with the only exception that the stirring time was limited to 2.5 h. The results are shown in the table below.

| pH | Delphinidin chloride |
|---|---|
| 6.0 | 0.60 mg/ml |
| 4.8 | 2.12 mg/ml |
| 4.1 | 2.03 mg/ml |

It can be seen that at pH values between 4 and 5, the solubility of the complexed delphinidin chloride increases by a factor of approximately 3 compared to a neutral pH.

Example 3

Preparation of a Solid According to the Invention

In this example, a complex according to the invention is formulated as a solid. For comparative purposes, a delphinidin/HPBCD complex and a delphinidin/starch formulation are prepared in the form of a solid.

Example 3.1

Delphinidin-SBE-β-CD 5 g of SEB-β-CD were dissolved in 40 ml of distilled water to give a clear solution. The pH of the solution was adjusted to 4.8 with 1 M HCl. 0.11 g of delphinidin chloride was then added and the mixture was stirred for 2 h at 27° C. in the dark. The homogeneous liquid was filtered under vacuum through a cellulose nitrate membrane filter of pore size 0.45 μm. The solution was frozen and subsequently freeze-dried at −48° C. and a pressure of approximately 10.3 Pa (77 mTorr). The lyophilizate was milled and sieved through a sieve of 0.3 mm mesh size.

Example 3.2

Delphinidin/HPBCD

This was processed in the same manner as Example 3.1, but a significant amount of material was filtered off during the filtration which indicates that the solubilization was significantly less effective than using SBE-β-CD according to Example 3.1.

Example 3.3

Delphinidin Starch Formulation 5 g of starch were suspended in 40 ml of distilled water. A white suspension was obtained. The pH of the solution was adjusted to 4.6 with 1 M HCl. 0.11 g of delphinidin chloride was then added and the mixture was stirred for 2 h at 27° C. in the dark. The resulting homogeneous liquid was freeze-dried and the solid milled and sieved, as in Example 3.1.

Example 3.1 is in accordance with the invention, while Examples 3.2 and 3.3 are comparative examples.

Example 4

Stability Trials

The solids according to Examples 3.1 to 3.3 were stored under the following conditions:
8 days at room temperature in brown, screwtop glass containers,
then 22 days at room temperature in glass containers in the dark in an oxygen atmosphere.

The latter 22 days of the storage mentioned above were conducted in glass vials with a volume of 20 ml. In each case, 250 mg of the samples previously already stored for 8 days were placed therein, and the vials were closed and sealed with a rubber stopper. By means of two injection needles, the head space of the vials was purged with pure oxygen. The samples were then stored in the dark.

The delphinidin content of the solids (calculated as delphinidin chloride and given in % by weight) was determined by the HPLC method described above. The results are given in the following table.

| | Time elapsed (days) | | | | |
|---|---|---|---|---|---|
| | Start | 2 | 8 | 19 | 30 |
| Example 3.1 | 1.69 | 1.52 | 1.55 | 1.40 | 0.93 |
| Example 3.2 | 1.30 | 1.20 | 1.14 | 1.03 | 0.68 |
| Example 3.3 | 1.60 | 1.59 | 1.56 | 1.53 | 1.15 |

The results show that a delphinidin complex can be prepared in accordance with the invention, which has high stability and thus good storage suitability even under a pure oxygen atmosphere. The complex also has good solubility in aqueous, particularly slightly acidic solutions, such that delphinidin may be formulated in accordance with the invention in a variety of ways. The stability of the solid according to the invention is just as good as a formulation with starch (Example 3.3), but this comparative example cannot be formulated as an aqueous solution.

Example 5

Stability Trials in Aqueous Solution

To determine the delphinidin chloride content in the delphinidin-containing solutions, a reversed-phase HPLC method was used similar to the one already described above. The following reagents were used in this case:
Purified water
Methanol for chromatography
Formic acid, p.a.
1 M hydrochloric acid as a volumetric solution.

The column used was a Waters×Bridge™ C18, 35 µl, 150 mm×4.6 mm.

The mobile phases were as follows:
Phase A: Water 770 ml, methanol 230 ml, formic acid 10 ml
Phase B: Water 50 ml, methanol 950 ml, formic acid 10 ml
The following gradient program was used:

| Time [min] | Percent phase B |
| --- | --- |
| 0 | 0 |
| 5 | 0 |
| 20 | 20 |
| 25 | 100 |

Stop time: 25 min
After-run time (post time): 8 min
Flow rate: 1 ml/min
Injection volume: 20 µl
Column temperature: 30° C. +/−2° C.
UV/Vis detector: 530 µm for the assay, 275 µm for the detection of impurities
Integrator: area
Solutions and Sample Preparation:
Dilution solution 1: Mixture of 100 ml of methanol and 2.6 ml of 1 M HCl
Dilution solution 2: Mixture of 100 ml of 50% methanol and 2.6 ml of 1 M HCl
Calibration solution: A reference solution of delphinidin was prepared by weighing 10 mg of delphinidin chloride into a 10 ml flask and dissolving in dilution solution 1. After dissolution, the solution was diluted approximately 10-fold with dilution solution 2 to produce an approximate concentration of 0.1 mg/ml.

The control calibration solution was prepared in the same manner. The calibration solutions were immediately analyzed by HPLC since delphinidin chloride is unstable in solution.

Preparation of the test solutions:
To determine the delphinidin content of an aqueous solution according to the invention, delphinidin/SBE-β-CD from Example 3.1 inventive) and delphinidin (comparative example were dissolved in 0.9% NaCl solution until a starting concentration (based on the delphinidin) of 1.584 mg/ml (inventive example) or 0.0216 mg/ml (comparative example) had been established. The solutions were prepared at room temperature and subsequently stored in the dark at 37° C. in closed vials.

The delphinidin content was determined after 1, 2, 3 and 4 h. The table below gives the content determined as a percentage of the starting concentration stated above.

| Time [h] | Non-complexed delphinidin | Delphinidin/SBE-β-CD |
| --- | --- | --- |
| 0 | 100% | 100% |
| 1 | 8.3% | 80.7% |
| 2 | 6.5% | 74.5% |
| 3 | 5.6% | 64.7% |
| 4 | 5.1% | 62.8% |

The determination of the delphinidin content in the samples was calculated with the aid of the Agilent ChemStation software using the calibration with the external standard described.

II. Effect of Delphinidin and the Delphinidin-SBE-β-CD Complex on Melanoma Cells Test Cell Lines In the in vitro experiments described below, the effect of the complex of delphinidin and sulfobutyl ether β-cyclodextrin (hereinafter delphinidin-SBE-β-CD) and delphinidin was investigated using the model human melanoma cell line A-375 [ATCC Catalog No. CRL-1619; Bruggen J., Sorg C. (1983) Detection of phenotypic differences on human malignant melanoma lines and their variant sublines with monoclonal antibodies. Cancer Immunol Immunother 15: 200-205].

The cell line was cultured at 37° C., 5% $CO_2$ in DMEM (Dulbecco's Modified Eagle's Medium from Gibco, Karlsruhe, Germany) supplemented with 10% FCS (Fetal Calf Serum) and antibiotics.

Example 6

Measurement of Induction of Apoptosis Using the Sub-G1 Peak Method

In the experiment according to Example 6, the effect of the substances investigated on the induction of apoptosis in the test cell line was investigated using the sub-G1 peak method, also commonly referred to as the "Nicoletti method" in the technical literature [Riccardi C. Nicoletti I. (2006) Analysis of apoptosis by propidium iodide staining and flow cytometry. Nat. Protoc. 1: 1458-1461].

The method is based on the lower DNA content of apoptotic cells compared to vital cells. A feature of apoptosis is the cleavage of DNA into short DNA fragments by endonucleases, whereby the content of low molecular weight DNA is increased and the proportion of high molecular weight DNA is reduced in apoptotic cells compared to vital cells. In induced lysis (permeabilization) of the cell membrane, the low molecular weight DNA fragments leak out from the apoptotic cells. If the cells are stained with propidium iodide (PI), a dye intercalating the DNA, apoptotic cells fluoresce less intensively than vital cells and the DNA content determined by flow cytometry in apoptotic cell nuclei appears as a broad, hypodiploid, more weakly fluorescing DNA peak (sub-G1 peak), which can be easily distinguished from the narrow DNA double peak of healthy cells with diploid DNA content. An example of this is provided by the histograms a and b shown in FIG. 1. Histogram a shows untreated, PI-stained cells. Propidium iodide has been incorporated into the DNA and fluoresces in two narrow peaks: the cells in the G1 phase (left peak) with single DNA content, and cells in the G2 phase (right peak) with double DNA content. A sub-G1 peak upstream of the left peak is virtually missing. Histogram b in contrast shows a broad sub-G1 peak. This shows the proportion of apoptotic cell nuclei after 24 hour treatment with delphinidin-SBE-β-CD.

To carry out the sub-G1 peak method according to Example 6, the cells were incubated for 24 hours with 10-3000 μg of delphinidin-SBE-β-CD per ml of cell suspension or 15-120 μM purified delphinidin chloride (hereinafter delphinidin Cl) per ml of cell suspension, where cells treated with the complex partner SBE-β-CD and also DMSO, and untreated cells, served as controls. For each individual experiment (control, delphinidin-SBE-β-CD, SBE-β-CD, delphinidin Cl), three 3 ml wells a on a well plate were prepared with cells. The cells were subsequently harvested by means of trypsinization, washed with ice-cold phosphate-buffered saline solution (PBS) and incubated for 1 hour with the staining buffer comprising 0.1% sodium citrate, 0.1% Triton X-100 and PI (40 μg/ml; Sigma-Aldrich, Taufkirchen, Germany), before then measuring and evaluating the DNA content of the cell nuclei by flow cytometry (FACSCalibur and CellQuest software; Becton Dickinson, Heidelberg). The mean was calculated from the respective triplicate measurements, where the measured values for the control cells served as reference for the t-test.

Figure 2A:
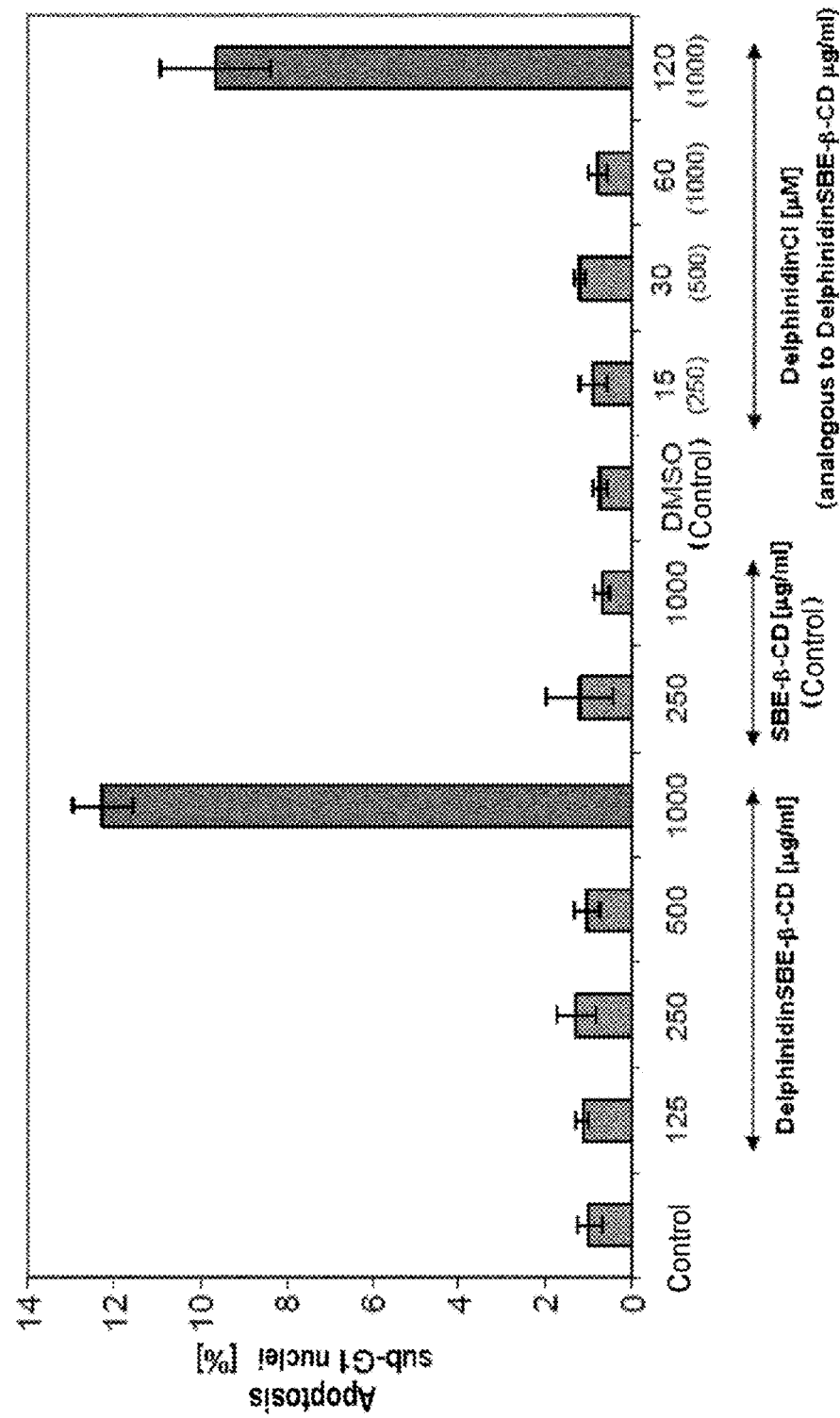
FIG. 2a shows the dose-dependent induction of apoptosis by delphinidin-SBE-β-CD and delphinidin Cl compared to the controls SBE-β-CD, DMSO and untreated A-375 cells at low cell confluence, determined by the sub-G1 peak method.

It is known that a low spontaneous apoptosis rate (background apoptosis) may occur during apoptosis measurements, wherein this effect particularly occurs if cells have already reached the growth plateau and suffer a lack of nutrients and oxygen. To take this into account, cells were measured which were in the exponential growth phase, in which the experiment was carried out in parallel both at low (low cell confluence) and higher cell density (higher cell confluence), of which the results processed graphically are shown in FIGS. 2a (low cell confluence) and 2b (higher cell confluence).

Figure 2B:
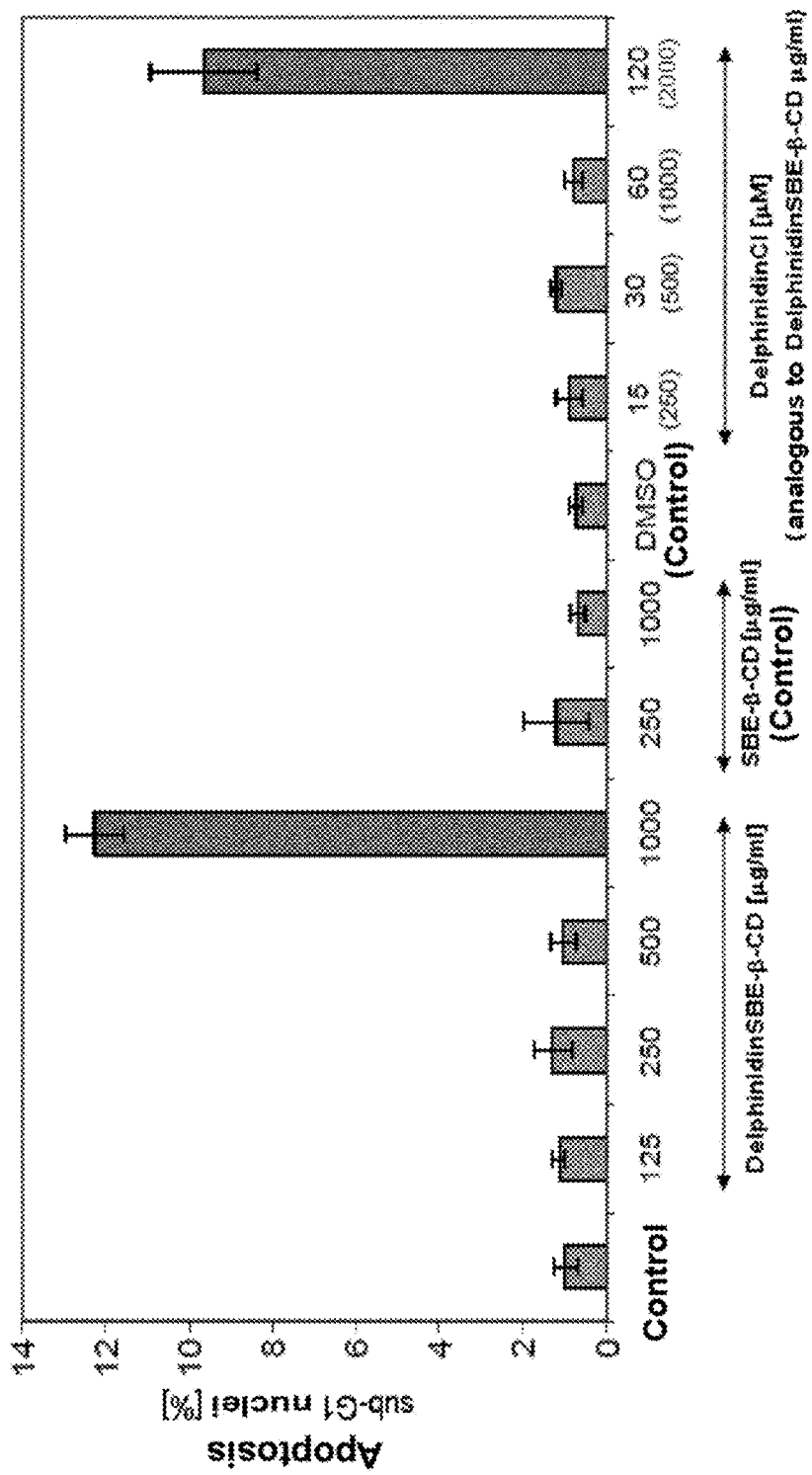
FIG. 2b shows the dose-dependent induction of apoptosis by delphinidin-SBE-β-CD compared to delphinidin Cl and the controls SBE-β-CD, DMSO and untreated A-375 cells at high cell confluence, determined by the sub-G1 peak method.

Experimental Results
- Purified delphinidin Cl shows a significant dose-dependent induction of apoptosis (cf. FIG. 2a at 120 μM);
- the delphinidin-SBE-β-CD complex shows a distinctly stronger induction of apoptosis (cf. FIG. 2a at 1000 μg/ml and FIG. 2b at 3000 μg/ml);
- whereas the complex partner SBE-β-CD and also DMSO shows no effect, analogous to the untreated control cells.

Example 7

Cell Viability Test

In the experiment according to Example 7, the effect of the substances investigated on the cell viability of the test cell line was quantified using the WST-1 assay (Water Soluble Tetrazolium) from Roche Diagnostics. The WST-1 assay is designed to detect an intact respiratory chain in cells, wherein vital cells having an intact mitochondrial succinate tetrazolium dehydrogenase system cause an enzymatic conversion of the weakly red-colored tetrazolium salt WST-1 (4-[3-(4-iodophenyl)-2-(4-nitrophenyl)-2H-5-tetrazolio]-1,3-benzene disulfonate) to the dark red formazan. This color change can be measured photometrically in a spectrophotometer and evaluated.

To carry out the WST-1 assay according to Example 7, the cells were incubated analogously to Example 6 for 24 hours with 10-3000 μg of delphinidin-SBE-β-CD per ml of cell suspension or 15-120 μM purified delphinidin Cl per ml of cell suspension, where cells treated with the complex partner SBE-β-CD and also DMSO, and untreated cells, served as controls. In the WST-1 assay, such as described in detail in Plötz et al. (2012), Mutual Regulation of Bcl-2 Proteins Independent of the BH3 Domain as Shown by the BH3-Lacking Protein Bcl-xAK, PLOS ONE, vol 7, issue 4, e34549, for example, the staining with calcein AM occurred on incubation with calcein (4 μM; e Bioscience, Frankfurt, Germany) in serum-free growth medium at 37° C. for 60 minutes as did washing with PBS, before the cell viability measurement was conducted by flow cytometry (see Example 5) in order to differentiate calcein-stained (living) cells from unstained (dead) cells.

Figure 3A:
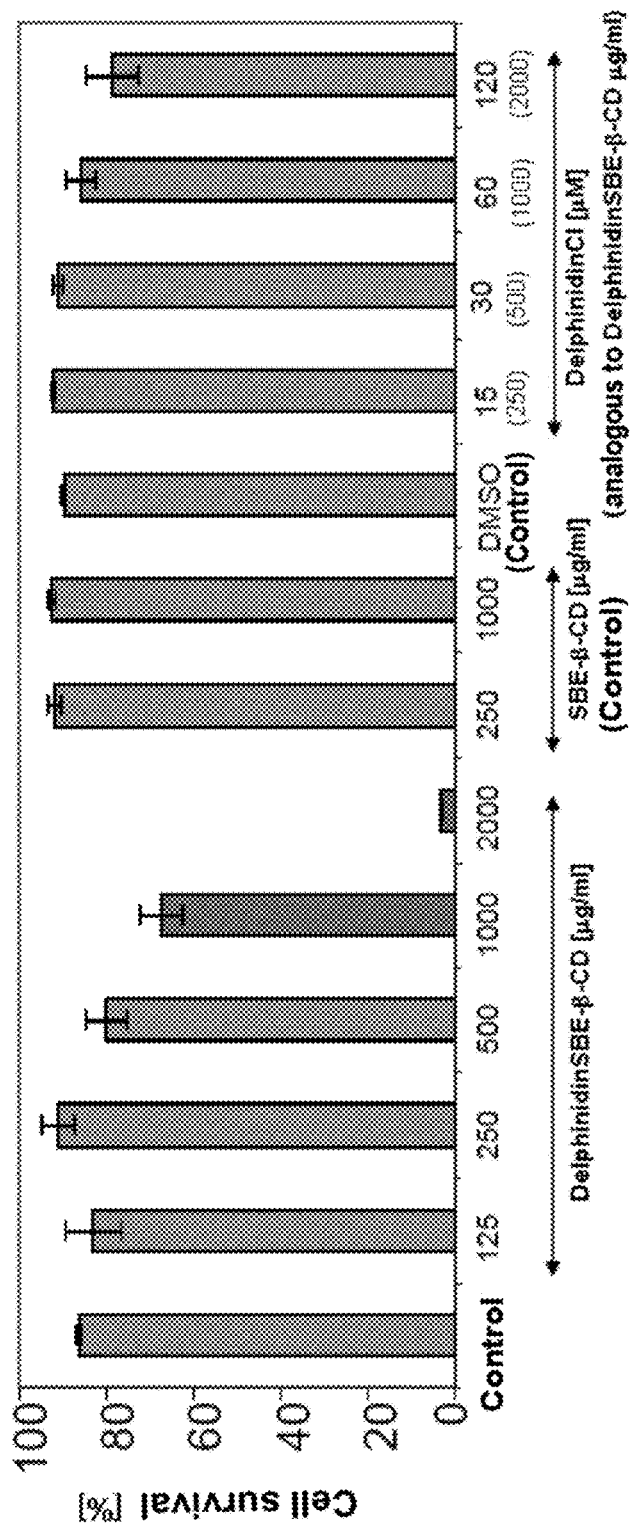
FIG. 3a shows the dose-dependent effect on cell viability of delphinidin-SBE-β-CD and delphinidin Cl compared to the controls SBE-β-CD, DMSO and untreated A-375 cells at low cell confluence, determined by the WST-1 assay.

Analogous to Example 6, the experiment in Example 7 was also carried out both at low (low cell confluence) and higher cell density (higher cell confluence), of which the results processed graphically are shown in FIGS. 3a (low cell confluence) and 3b (higher cell confluence).

Figure 3B:
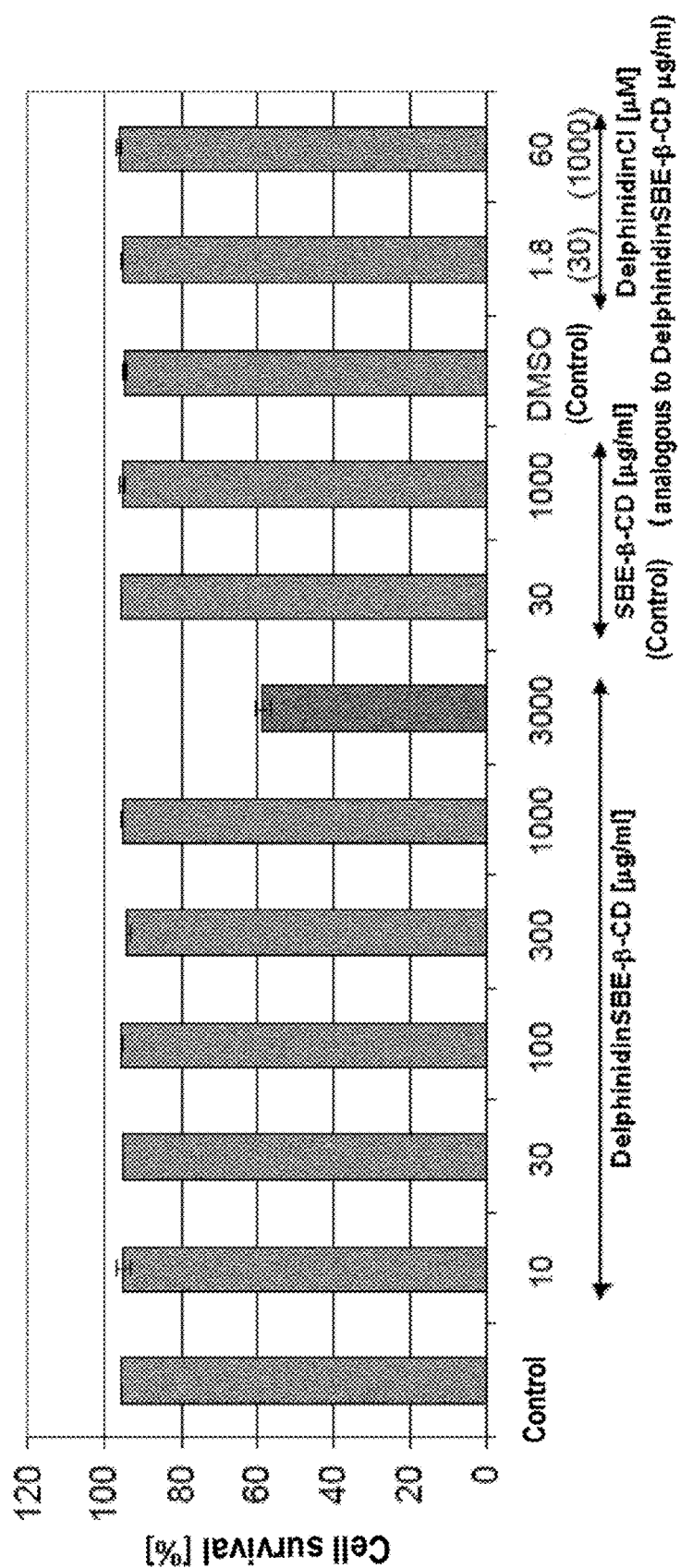
FIG. 3b shows the dose-dependent effect on cell viability of delphinidin-SBE-β-CD compared to delphinidin Cl and the controls SBE-β-CD, DMSO and untreated A-375 cells at high cell confluence, determined by the WST-1 assay.

Experimental Results
- Purified delphinidin Cl shows a loss of vital cells with increasing dose at low cell confluence (cf. FIG. 3a);
- delphinidin-SBE-β-CD complex causes a distinctly higher and significant loss of cell vitality (cf. FIG. 3a at 1000 μg/ml and 2000 μg/ml and FIG. 3b at 3000 μg/ml);
- whereas the complex partner SBE-β-CD and also DMSO shows no effect, analogous to the untreated control cells.

Figure 4:
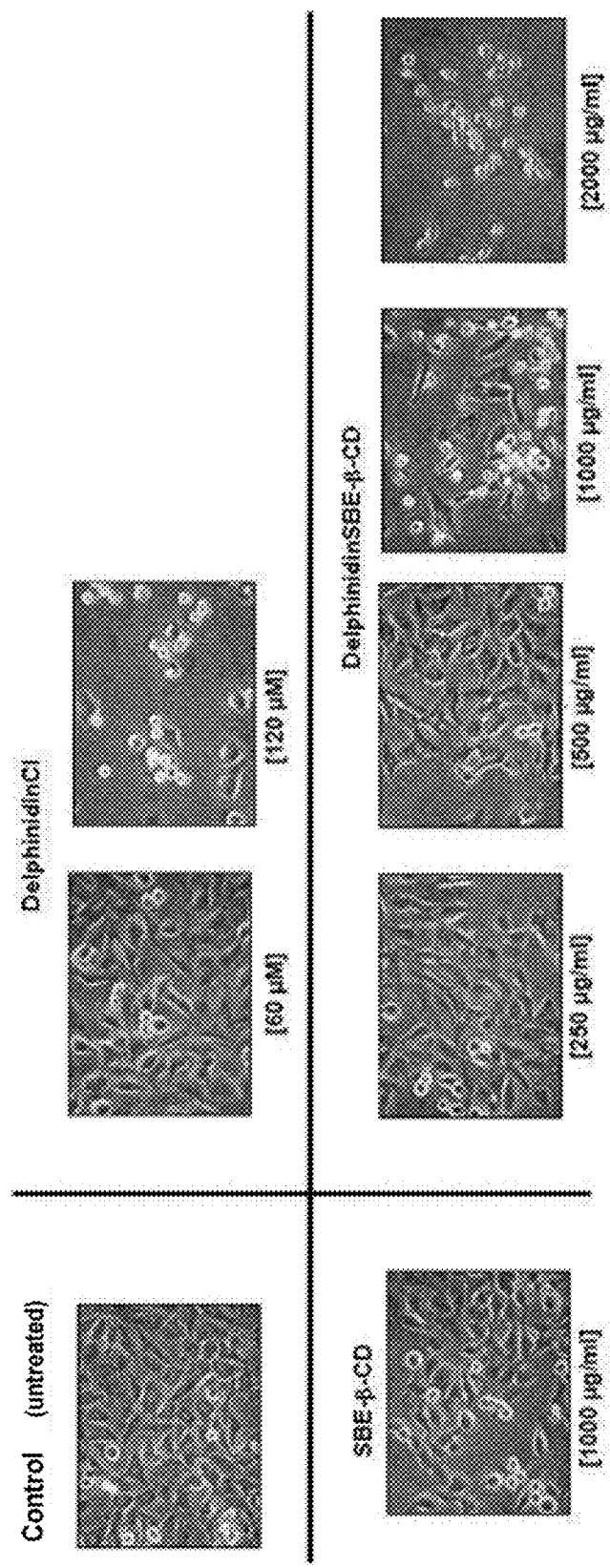
FIG. 4 shows micrographs of untreated A-375 cells and A-375 cells treated with delphinidin-SBE-β-CD, delphinidin Cl and SBE-β-CD.

The effect of the loss of vital cells beyond induction of apoptosis (Example 6) is also reflected in the morphology of the cells under microscopic analysis after 24 hours of treatment, which cells at high concentrations of delphinidin Cl or delphinidin-SBE-β-CD become globular and/or detached, as is evident from the micrographs in FIG. 4.

Example 8

Real-Time Cell Analysis—RTCA

The cell number and cell proliferation at the same active ingredient investigation, analogous to Examples 6 and 7, was recorded in real time using the xCELLigence system (Roche Diagnostics, Mannheim, Germany). The xCELLigence system is a microelectronic biosensor system for cell-based, label-free analyses which provides dynamic cell data in real time. The culture plates of the xCELLigence system are equipped with microelectrodes at the bottom of each well to measure changes in electrical impedance. Quantitative changes in impedance correlate with the number and strength of the cell contacts using the underlying electrodes.

Figure 5:
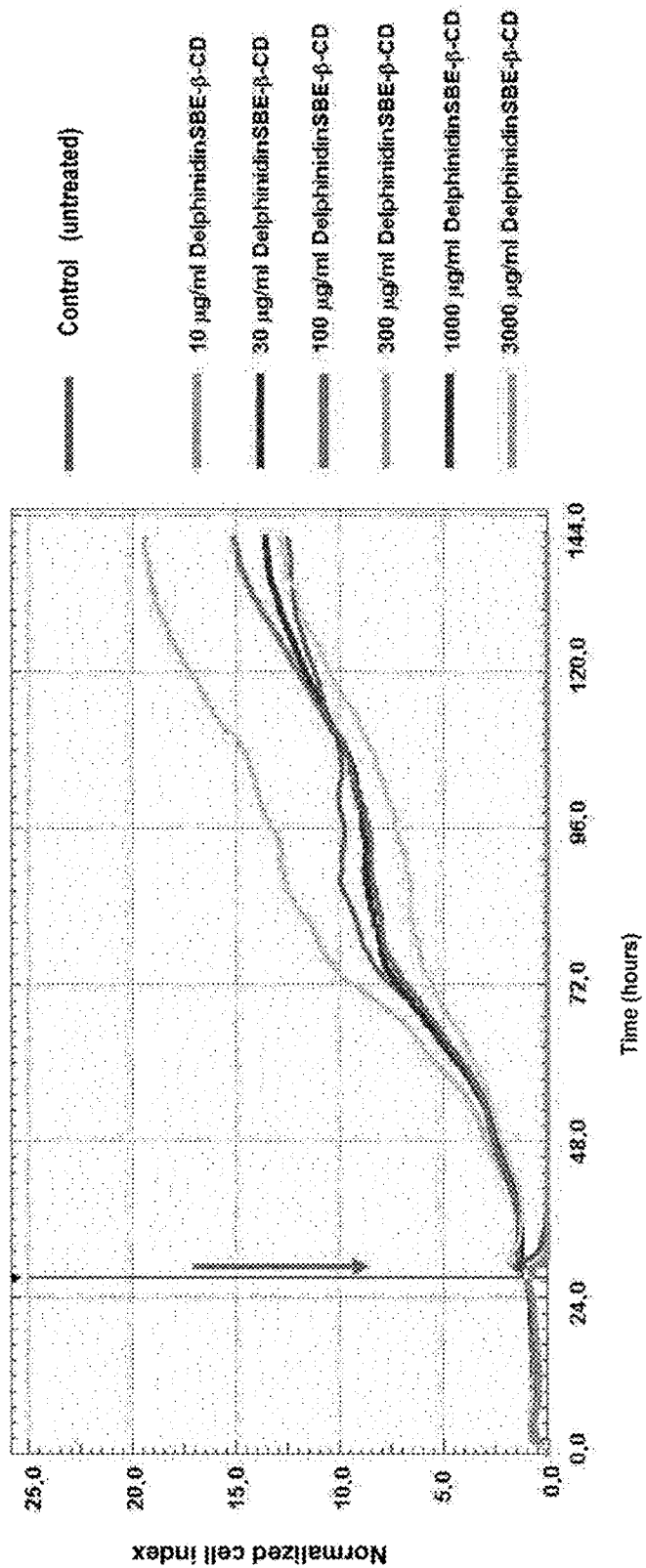
FIG. 5 shows cell number and cell proliferation (real-time cell monitoring) of high cell confluence A-375 cells treated with delphinidin-SBE-β-CD compared to untreated cells, using the xCELLigence system.
Figure 6:
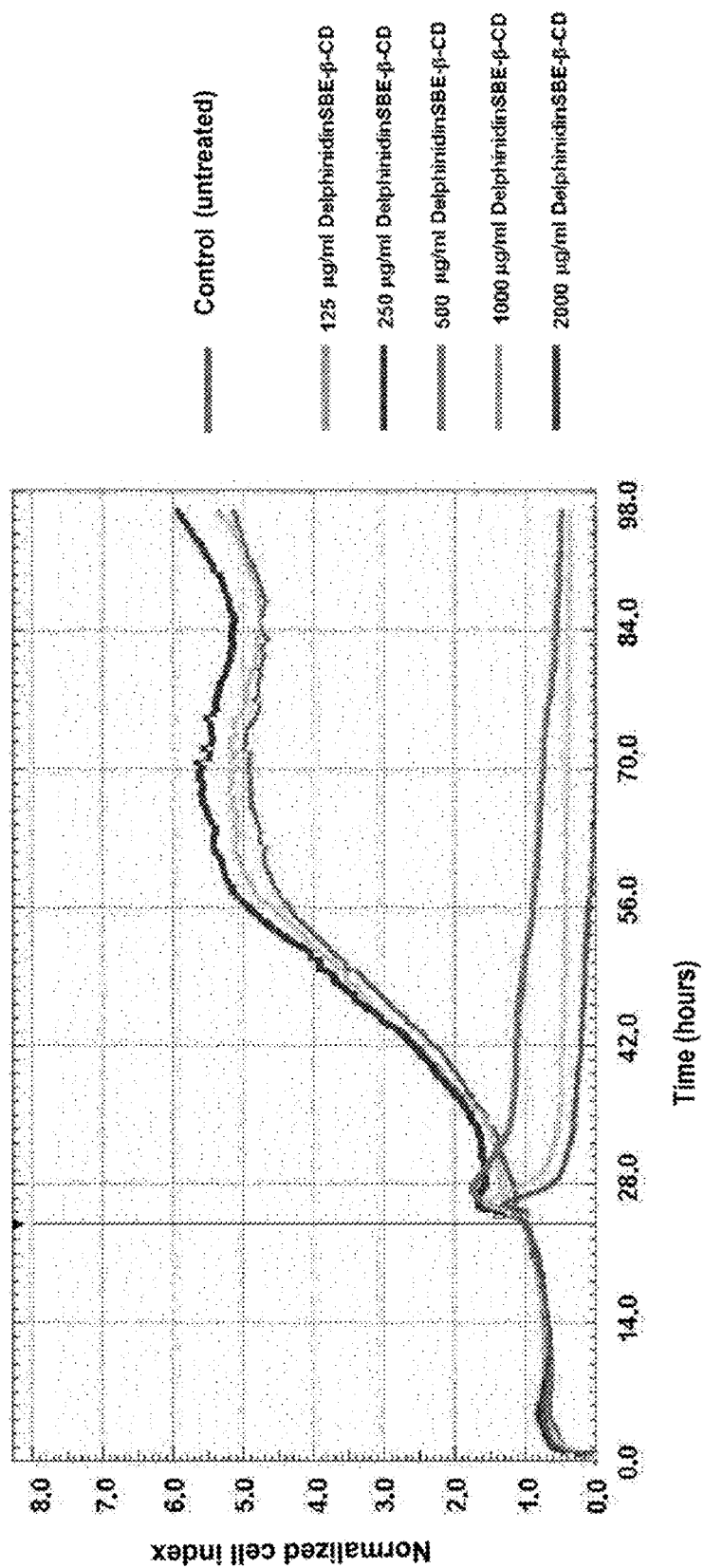
FIG. 6 shows cell number and cell proliferation (real-time cell monitoring) of low cell confluence A-375 cells treated with delphinidin-SBE-β-CD compared to untreated cells, using the xCELLigence system.

Delphinidin-SBE-β-CD shows a complete decline in cell proliferation (cf. FIGS. 5 and 6) in accordance with the high rates of apoptosis (Example 6) and the loss of cell vitality (Example 7) and particularly strong antiproliferative effects from a concentration of 1000 μg/mL in FIG. 5 and a complete blockade of cell proliferation from 500 μg/ml in FIG. 6.

Figure 7:
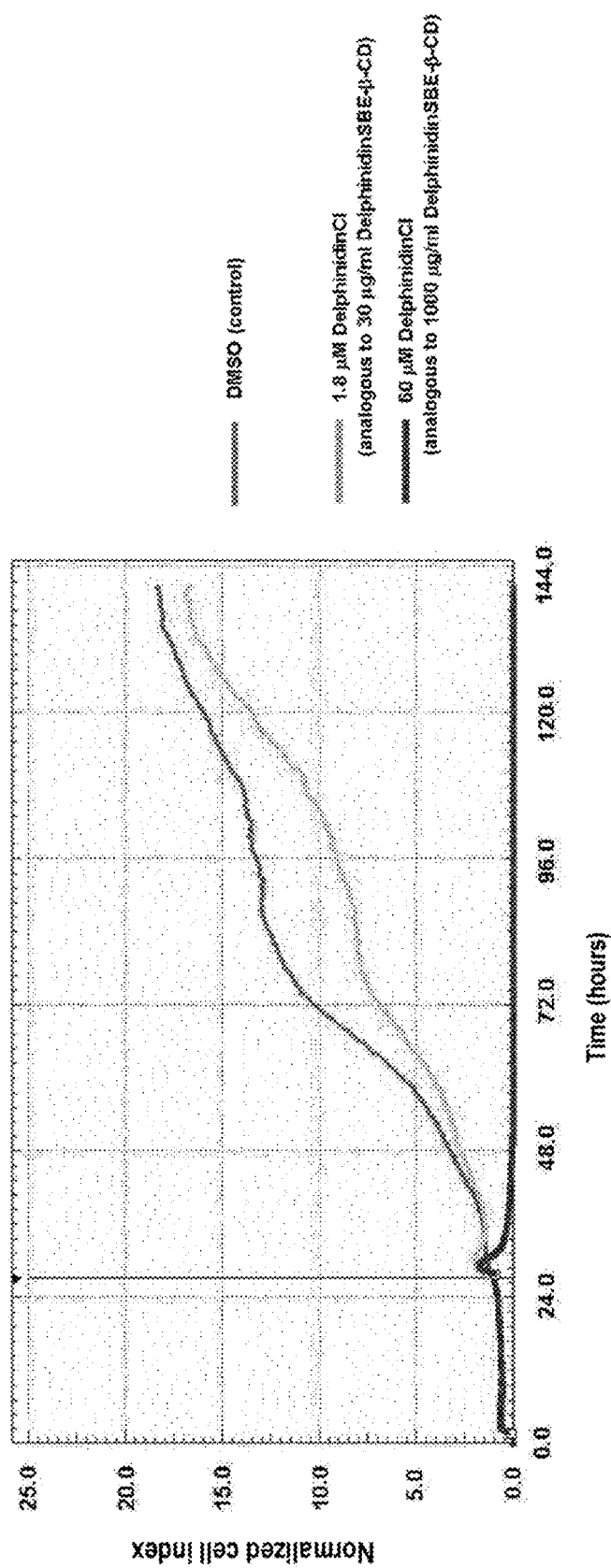
FIG. 7 shows cell number and cell proliferation (real-time cell monitoring) of high cell confluence A-375 cells treated with delphinidin Cl compared to untreated cells, using the xCELLigence system.
Figure 8:
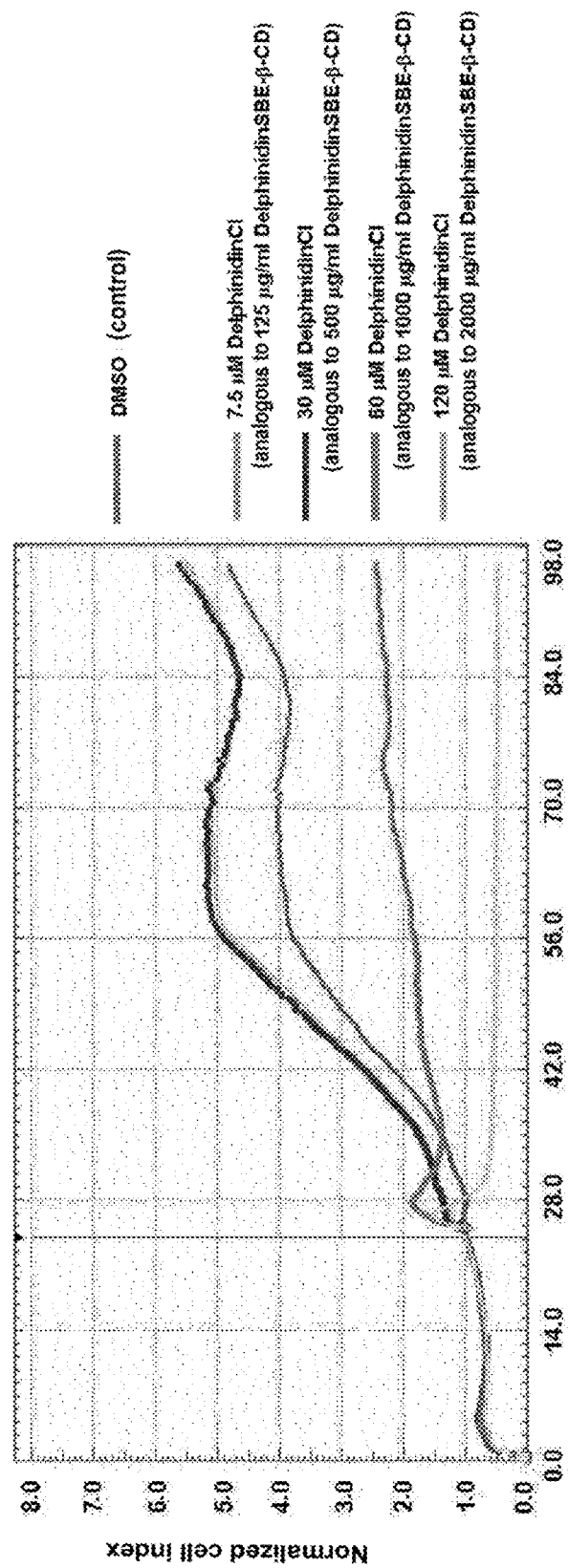
FIG. 8 shows cell number and cell proliferation (real-time cell monitoring) of low cell confluence A-375 cells treated with delphinidin Cl compared to untreated cells, using the xCELLigence system.
Figure 9:
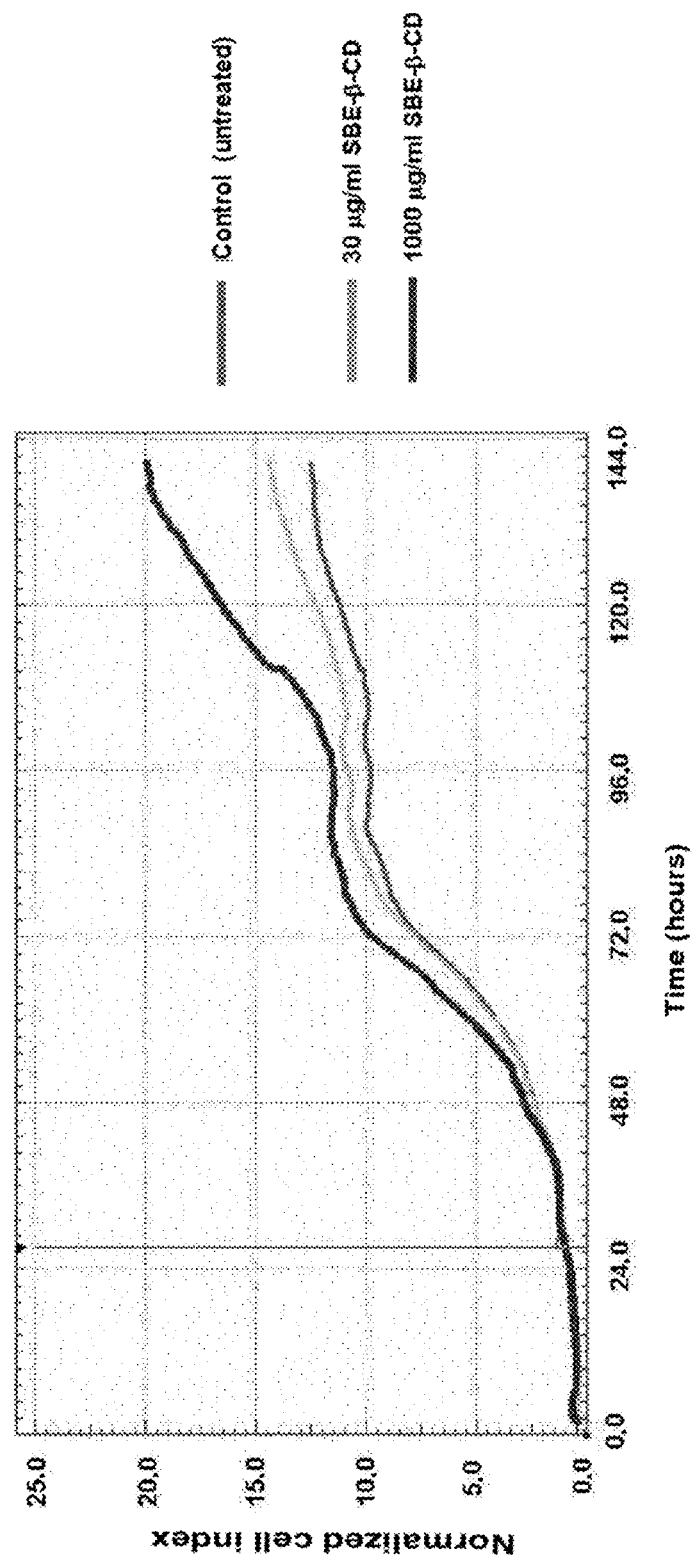
FIG. 9 shows cell number and cell proliferation (real-time cell monitoring) of high cell confluence A-375 cells treated with SBE-β-CD compared to untreated cells, using the xCELLigence system.
Figure 10:
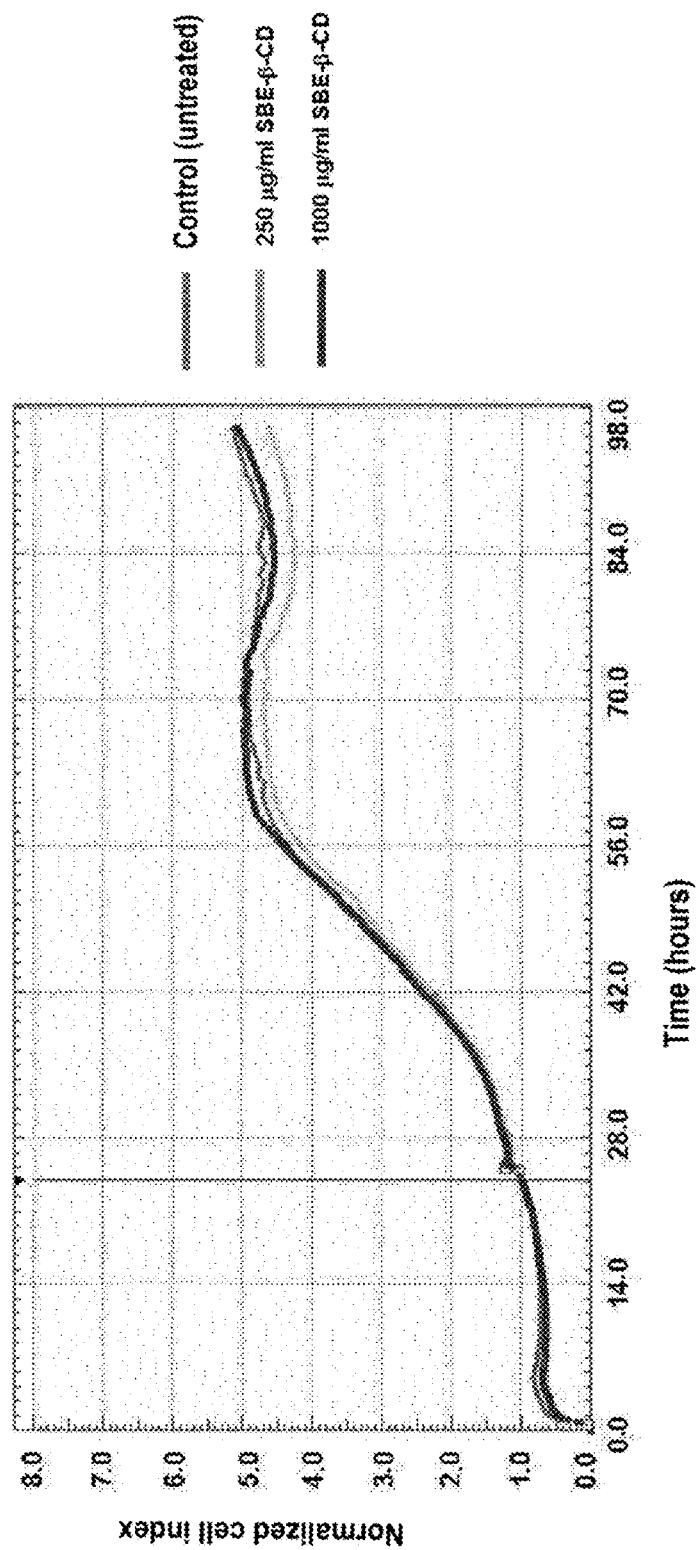
FIG. 10 shows cell number and cell proliferation (real-time cell monitoring) of low cell confluence A-375 cells treated with SBE-β-CD compared to untreated cells, using the xCELLigence system.

Similarly strong antiproliferative effects are seen with delphinidin Cl at 60-120 μM (cf. FIGS. 7 and 8) while, as expected, the untreated cells and the DMSO control behaved in an almost neutral manner (cf. FIGS. 7-10), i.e. the antiproliferative effects described previously are uniquely attributable to the investigated active ingredients delphinidin-SBE-β-CD and delphinidin Cl.

III. Effect of Delphinidin and the Delphinidin-SBE-β-CD Complex in Combination with TRAIL on Melanoma Cells Test Cell Line and Methods Used The same cell line and method was used in the experiments as in the preceding section II.

Example 9

Measurement of Induction of Apoptosis Using the Sub-G1 Peak Method

Figure 11A:
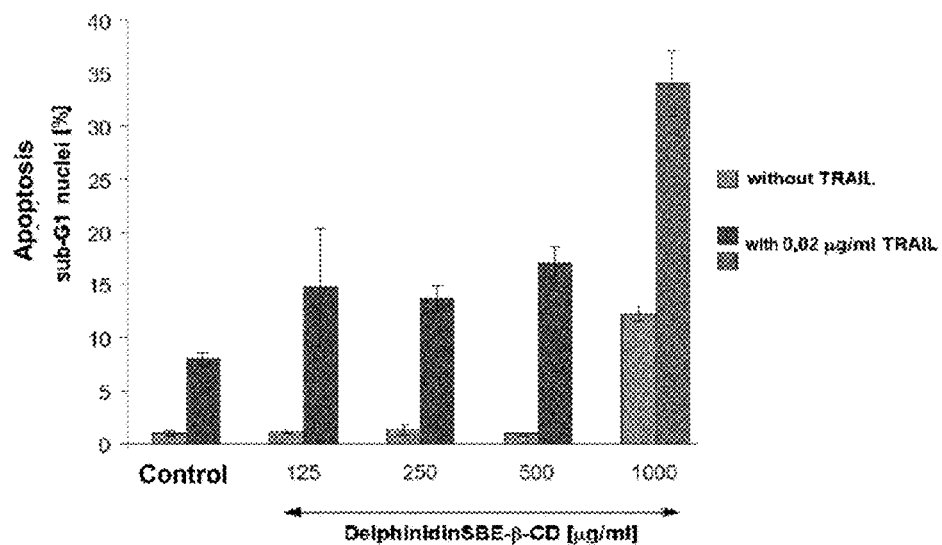
FIG. 11a shows the induction of apoptosis by delphinidin-SBE-β-CD with and without TRAIL compared to the controls (untreated cells or cells treated only with TRAIL) at low cell confluence, determined by the sub-G1 peak method.
Figure 11B:
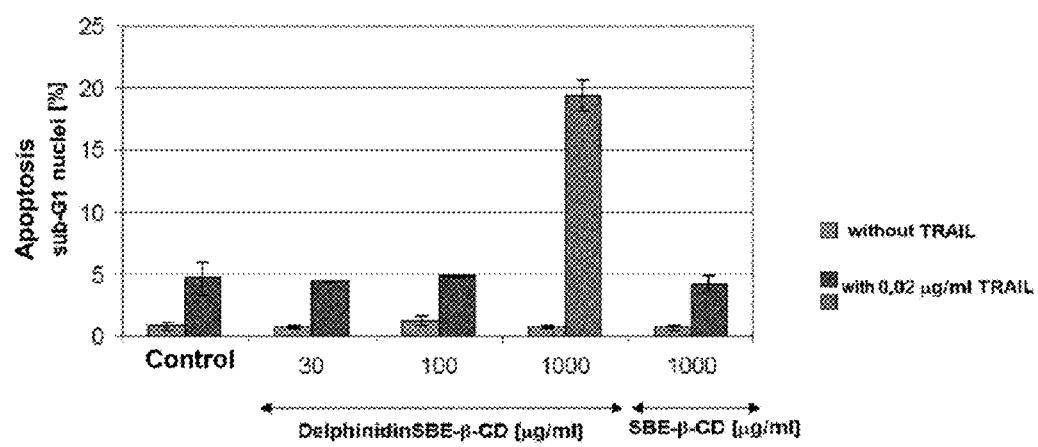
FIG. 11b shows the induction of apoptosis by delphinidin-SBE-β-CD with and without TRAIL compared to the controls (untreated cells or cells treated only with TRAIL, cells treated with SBE-β-CD) at high cell confluence, determined by the sub-G1 peak method.

In the experiment according to Example 9, the effect of the delphinidin-SBE-β-CD complex in combination with the proapoptotic death ligand TRAIL was investigated using the sub-G1 peak method, against which the cell line A-375 has only moderate apoptosis sensitivity. To carry out the sub-G1 peak method according to Example 9, the cells were incubated for 24 hours with 30-1000 µg of delphinidin-SBE-β-CD per ml of cell suspension with and without 0.02 µg of TRAIL per ml of cell suspension, where cells treated with the complex partner SBE-β-CD and untreated cells served as controls. The experiments were carried out in parallel both at low (low cell confluence) and higher cell density (higher cell confluence), of which the results processed graphically are shown in FIGS. 11a (low cell confluence) and 11b (higher cell confluence).

Experimental Results

In the combination of delphinidin-SBE-β-CD with TRAIL, the induction of apoptosis is increased with respect to delphinidin-SBE-β-CD alone at all delphinidin-SBE-β-CD concentrations investigated;

an increase in induction of apoptosis is likewise significantly increased for delphinidin-SBE-β-CD with TRAIL with respect to TRAIL alone at higher delphinidin-SBE-β-CD concentrations;

whereas the complex partner SBE-β-CD is at control level.

Example 10

Cell Viability Test

In the experiment according to Example 10, the cell viability of the test cell line was investigated analogously to Example 7, with the difference that the cells were exposed to the combination of delphinidin-SBE-β-CD complexes and TRAIL.

To carry out the assay analogously to Example 7, the cells were incubated for 24 hours with 30-1000 µg of delphinidin-SBE-β-CD per ml of cell suspension with and without 0.02 µg/ml of TRAIL per ml of cell suspension, where cells treated with the complex partner SBE-β-CD and untreated cells served as controls.

Figure 12A:
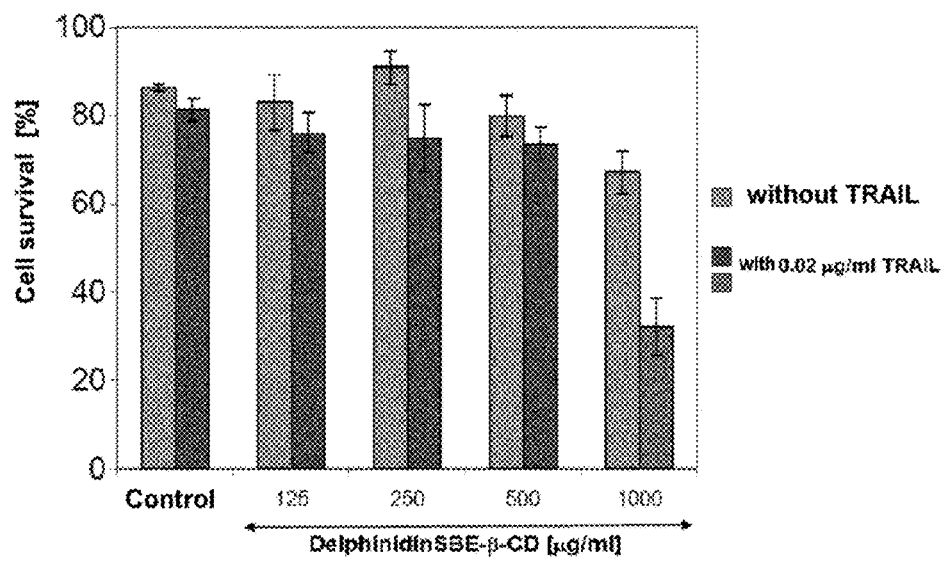
FIG. 12a shows the effect on cell viability of delphinidin-SBE-β-CD with TRAIL compared to delphinidin-SBE-β-CD alone and the controls (untreated cells or cells treated only with TRAIL) at low cell confluence, determined by the WST-1 assay.
Figure 12B:
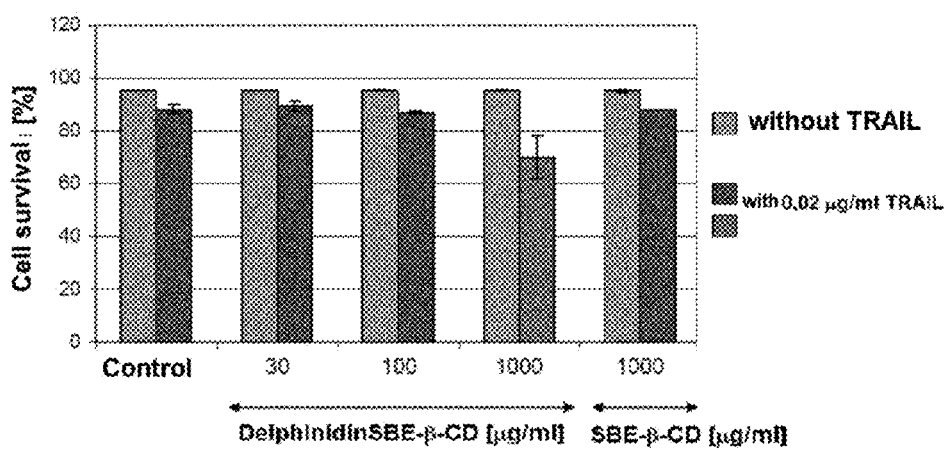
FIG. 12b shows the effect on cell viability of delphinidin-SBE-β-CD with TRAIL compared to delphinidin-SBE-β-CD alone and the controls (untreated cells or cells treated only with TRAIL, cells treated with SBE-β-CD) at high cell confluence, determined by the WST-1 assay.

The experiment in Example 10, analogous to Example 9, was also carried out both at low (low cell confluence) and higher cell density (higher cell confluence), of which the results processed graphically are shown in FIGS. 12a (low cell confluence) and 12b (higher cell confluence)

Experimental Results

In the combination of delphinidin-SBE-β-CD with TRAIL, the cell vitality decreases with respect to delphinidin-SBE-β-CD alone at all delphinidin-SBE-β-CD concentrations investigated;

a decrease in cell vitality is likewise evident which the combination of delphinidin-SBE-β-CD with TRAIL with respect to TRAIL alone at higher delphinidin-SBE-β-CD concentrations;

whereas the complex partner SBE-β-CD is at control level.

Figure 13:
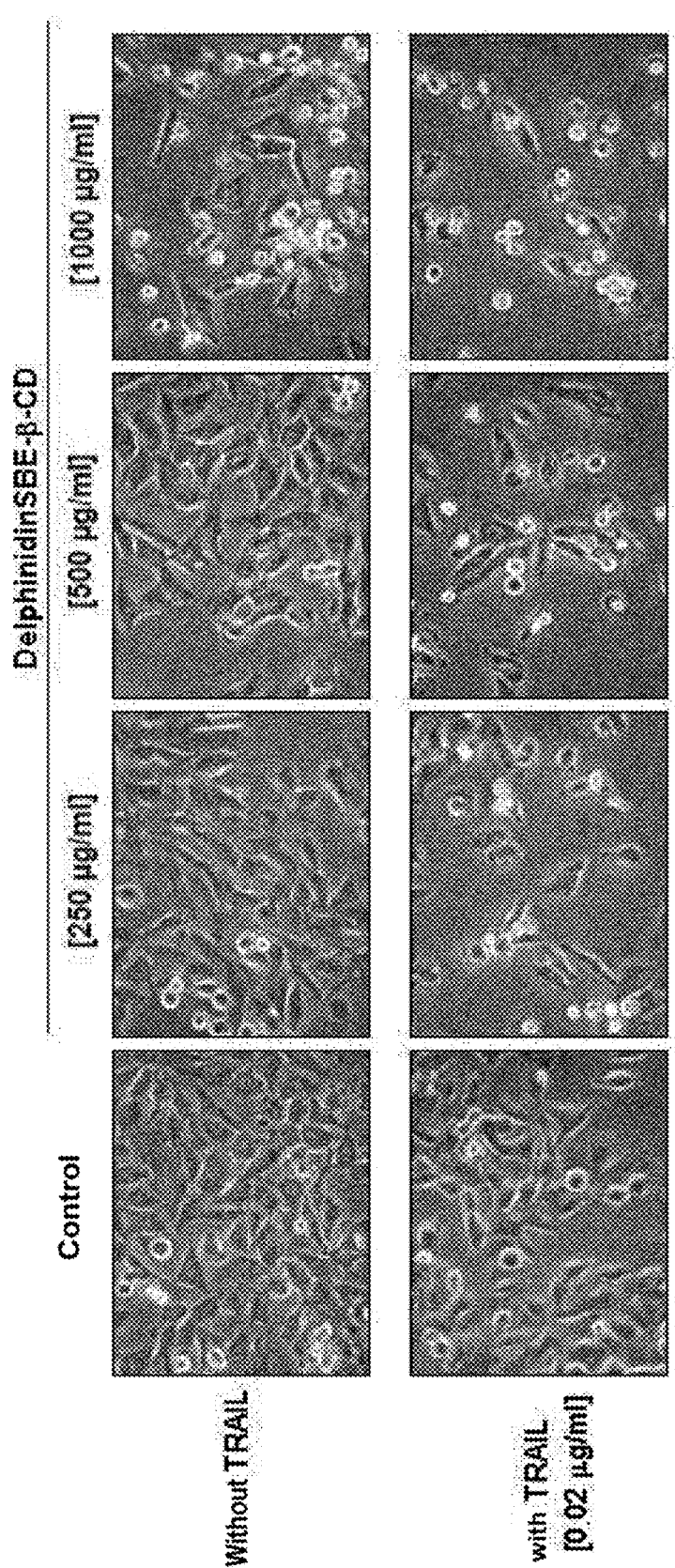
FIG. 13 shows micrographs of untreated A-375 cells, A-375 cells treated only with TRAIL, treated only with delphinidin-SBE-β-CD and treated with delphinidin-SBE-β-CD and TRAIL.

The effect of the loss of vital cells beyond induction of apoptosis (Example 9) is also reflected in the morphology of the cells under microscopic analysis 24 hours after treatment, where use of TRAIL in addition to delphinidin-SBE-β-CD causes the cells to become even more globular and/or detached, as is evident from the micrographs in FIG. 13.

Example 11

Real-Time Cell Analysis—RTCA

The cell number and cell proliferation at the same active ingredient investigation, analogous to Examples 9 and 10 and additionally supplemented by the combination of delphinidin Cl with and without TRAIL, was recorded in real time using the xCELLigence system (Roche Diagnostics, Mannheim, Germany).

Figure 14:
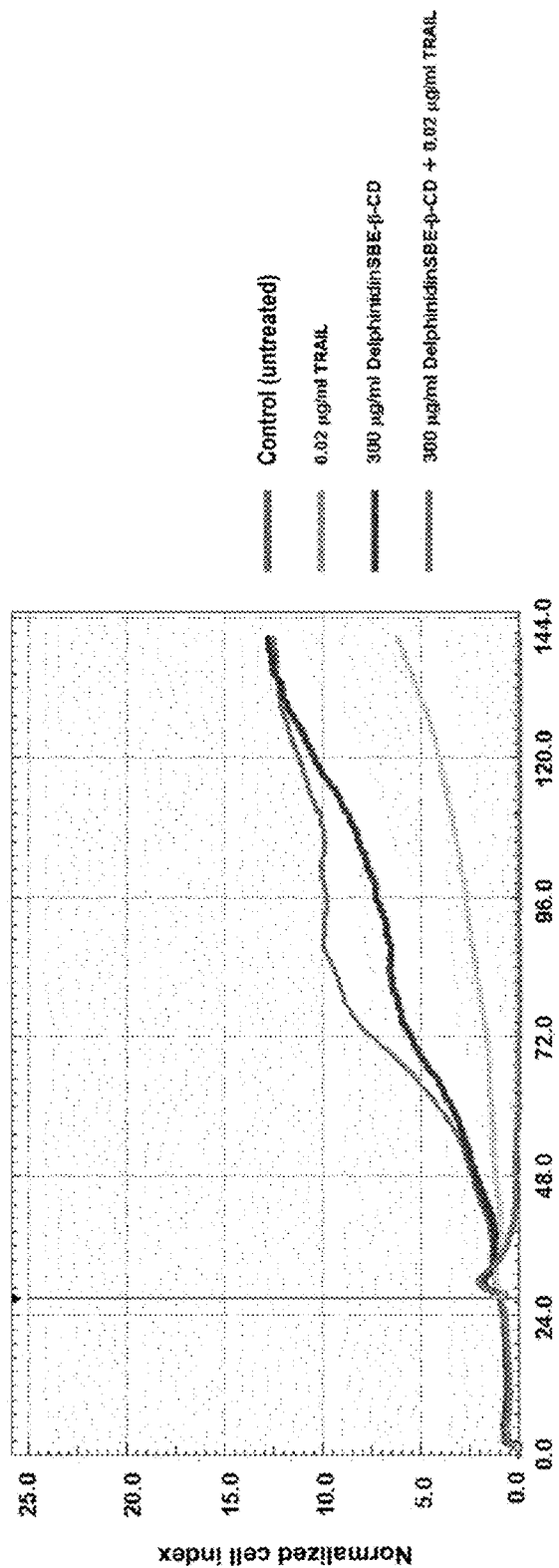
FIG. 14 shows cell number and cell proliferation (real-time cell monitoring) of high cell confluence A-375 cells treated with TRAIL, delphinidin-SBE-β-CD, TRAIL and delphinidin-SBE-β-CD compared to untreated cells, using the xCELLigence system.
Figure 15:
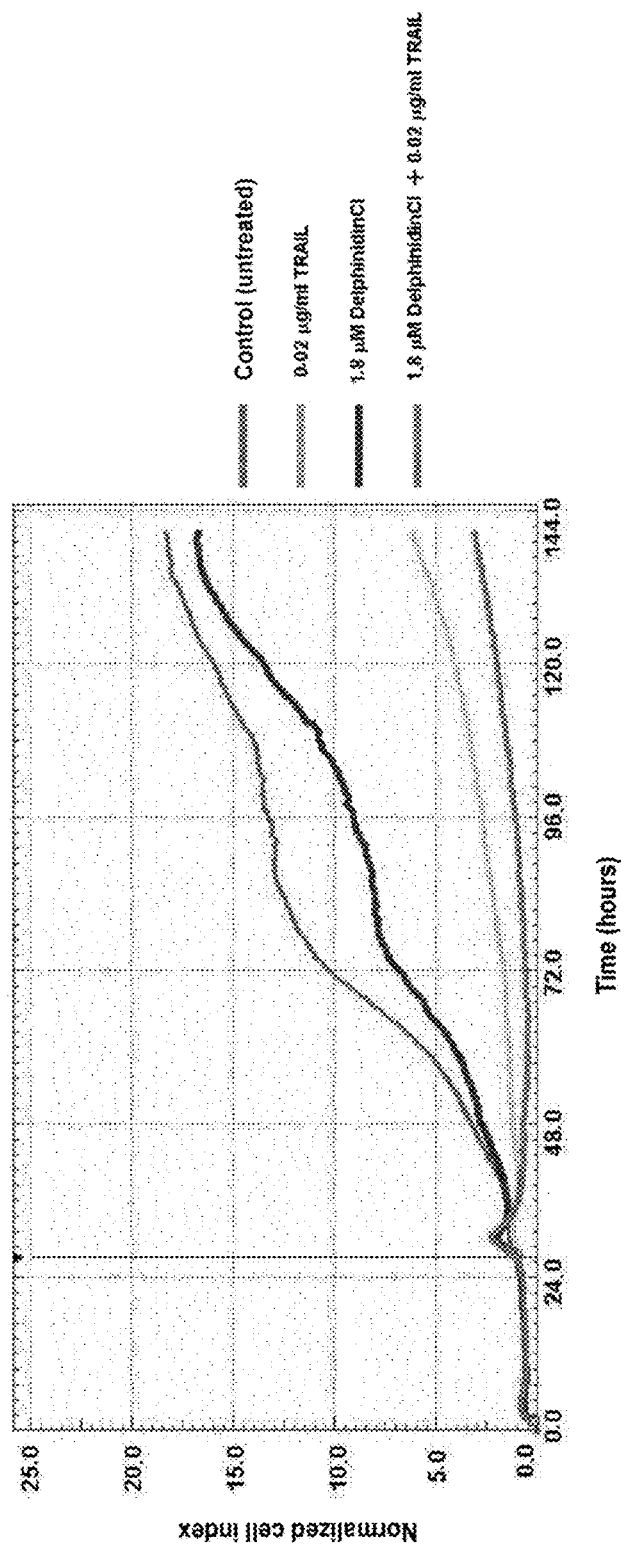
FIG. 15 shows cell number and cell proliferation (real-time cell monitoring) of high cell confluence A-375 cells treated with TRAIL, delphinidin Cl, TRAIL and delphinidin Cl compared to untreated cells, using the xCELLigence system.
Figure 16:
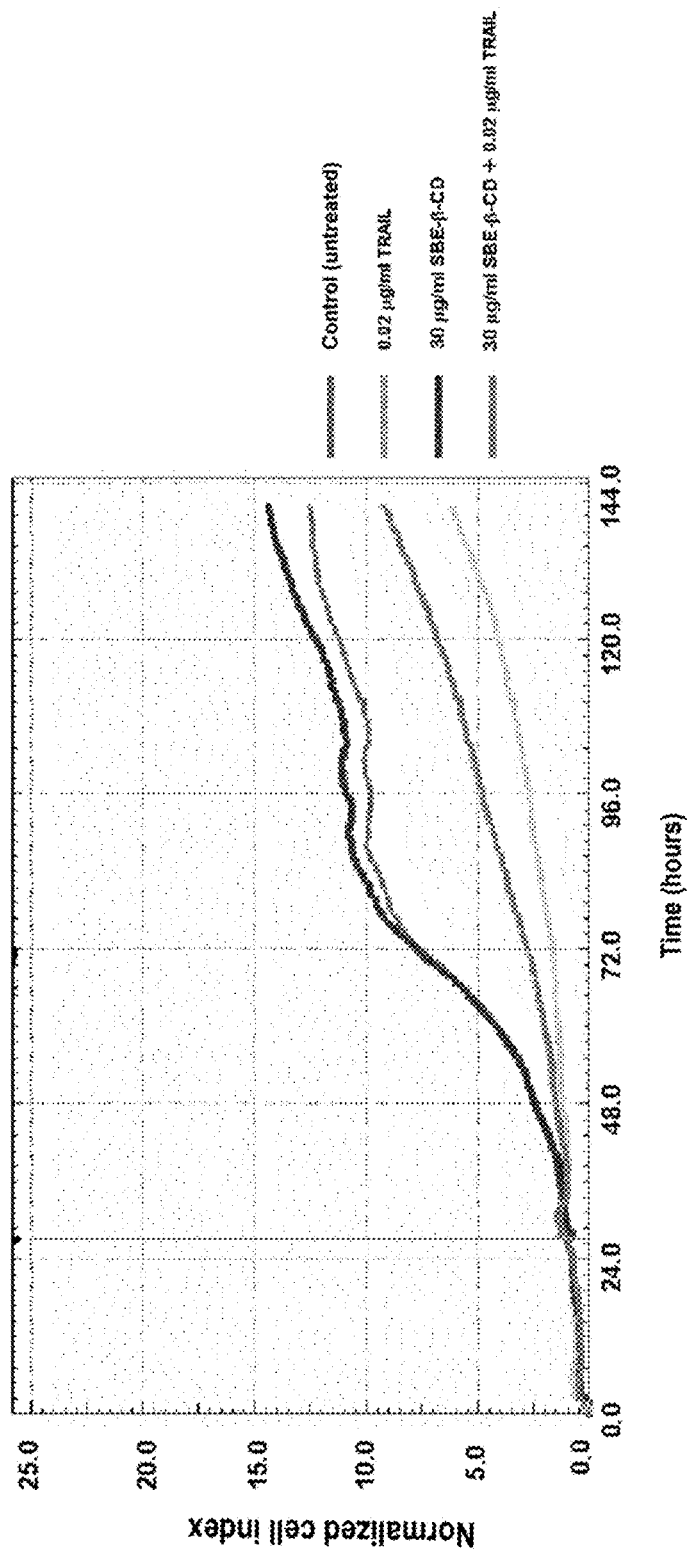
FIG. 16 shows cell number and cell proliferation (real-time cell monitoring) of high cell confluence A-375 cells treated with TRAIL (0.02 µg/ml), SBE-β-CD (30 µg/ml), TRAIL (0.02 µg/ml) and SBE-β-CD (30 µg/ml) compared to untreated cells, using the xCELLigence system.
Figure 17:
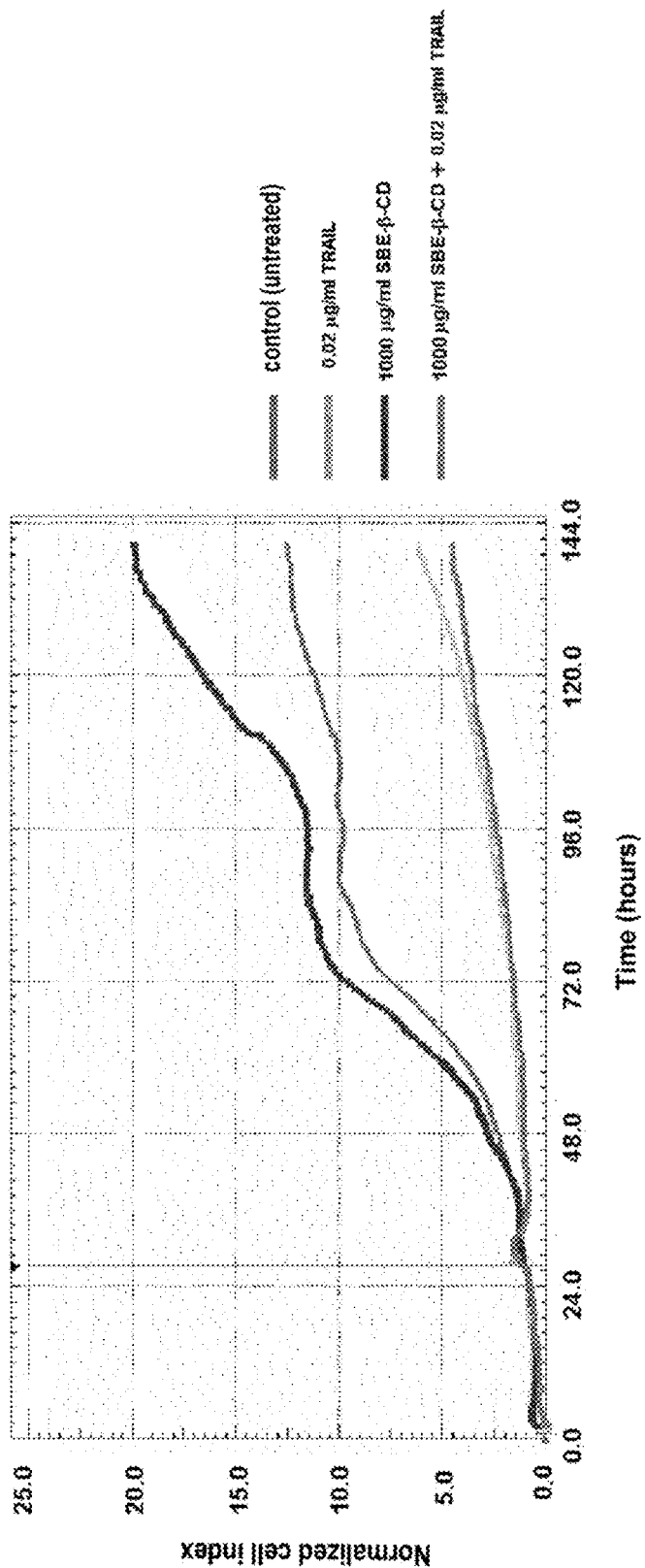
FIG. 17 shows cell number and cell proliferation (real-time cell monitoring) of high cell confluence A-375 cells treated with TRAIL (0.02 µg/ml), SBE-β-CD (1000 µg/ml), TRAIL (0.02 µg/ml) and SBE-β-CD (1000 µg/ml) compared to untreated cells, using the xCELLigence system.

Delphinidin-SBE-β-CD in combination with TRAIL shows synergistic and stronger blocking of cell proliferation (cf. FIG. 14) in accordance with the increased rates of apoptosis (Example 9) and greater loss of cell vitality (Example 10) compared to delphinidin-SBE-β-CD alone. Stronger blocking of cell proliferation can also be observed in the combination of delphinidin Cl with TRAIL compared to TRAIL alone and delphinidin alone (cf. FIG. 15). No intensification of TRAIL sensitivity by SBE-β-CD could be observed (cf. FIGS. 16 and 17), i.e. the intensification of antiproliferative effects described above are uniquely attributable to the active ingredient delphinidin investigated in the delphinidin-SBE-β-CD in combination with TRAIL.

IV. Cytotoxicity Investigations—Effect of Delphinidin and the Delphinidin-SBE-β-CD Complex on Cell Vitality

Example 12

Effect of Delphinidin and the Delphinidin-SBE-β-CD Complex on Vitality of Human Fibroblasts and Endothelial Cells Cells Used The cells used were primary, even isolated fibroblasts and microvascular endothelial cells from human donor skin.

To isolate the fibroblasts, the tissue cell structure was dissolved by means of a one-hour incubation with trypsin-EDTA solution. To stop the cell detachment reaction, stop medium was added to the skin. The piece of skin was then swirled twice in PBS resulting in a suspension of fibroblasts. The fibroblasts obtained were centrifuged at 4° C. for 5 min at 100 revolutions per minute and were used after quantification.

The human dermal microvascular endothelial cells were obtained by the standard method known to those skilled in the art of Hewett and Murray (1993) [Hewett P. W. and Murray J. C. (1993) Immunomagnetic purification of human microvessel endothelial cells using Dynabeads coated monoclonal antibodies to PECAM-1. *Eur J Cell Biol* 62: 451-454; Hewett P. W. & Murray J. C. (1993) Human microvessel endothelial cells: Isolation, culture and characterization. *In Vitro Cell Biol*: 823-830].

Measurement Method Used

In the experiments according to Example 12, the effect of the substances investigated on the vitality of human fibroblasts and endothelial cells was investigated using the ATP luminescence assay, which is known to those skilled in the art and is briefly summarized below for the sake of completeness.

After cell death, due to the effect of a cytotoxic active ingredient for example, the intracellular ATP content decreases to a large degree due to degradation mediated by ATPases. By the inhibition of endogenous ATPases, the ATP content liberated by lysis can thus be used as a measure for the number of vital cells. For the quantification, the liberated ATP is coupled to a reaction catalyzed by the enzyme luciferase, in which the ATP-dependent oxidation of the substrate luciferin to oxyluciferin, carbon dioxide, AMP and inorganic phosphate takes place in the presence of $Mg^{2+}$, with release of light. The amount of light released correlated with the ATP content is measured and provides a directly quantifiable conclusion about the vitality of the cells investigated. This is measured in RLU (relative light units), an independent unit which reflects the amount of ATP in the sample. Kits and instruments for ATP determination are known to those skilled in the art, for example, the ATP test kit from Biothema, AB, Haning, Sweden, and the portable luminometer Lumino® from STRATEC Biomedical Systems AG, Birkenfeld, Germany. To determine intracellular ATP, 50 µl of the sample to be investigated are usually pipetted into a glass tube, 50 µl of the extractant reagent B/S added thereto for cell lysis and 400 µl of ATP-HS reagent added and, after subsequent mixing, the sealed tube is placed in the luminometer for automatic measurement and evaluation of the light emission.

Prior to the treatment with active ingredient and application of the ATP luminescence assay, the human fibroblasts or endothelial cells with Dulbecco's Modified Eagle's Medium (DMEM medium) were seeded in the present case in 96-well microtiter plates (5000 cells/well) and cultured for 3 days. After this adhesion and growth phase of the cells in an incubator, the substance treatment was carried out at time intervals of Day 1-Day 4 (endothelial cells) and 4 h, 24 h, h and 96 h (fibroblasts), where active ingredient delphinidin Cl or delphindin-SBE-β-CD complex dissolved in 100 µl of DMEM medium was added to 3 wells respectively at various concentrations (0.1 µM; 3.2 µM; 100 µM). Cells with substance-free medium were used as a reference control. Depletion of the substances occurred after 3 hours, followed by washing with Dulbecco's phosphate-buffered saline (PBS). The endpoint measurement was carried out using the WST-1 assay already mentioned in Example 7.

Figure 18:
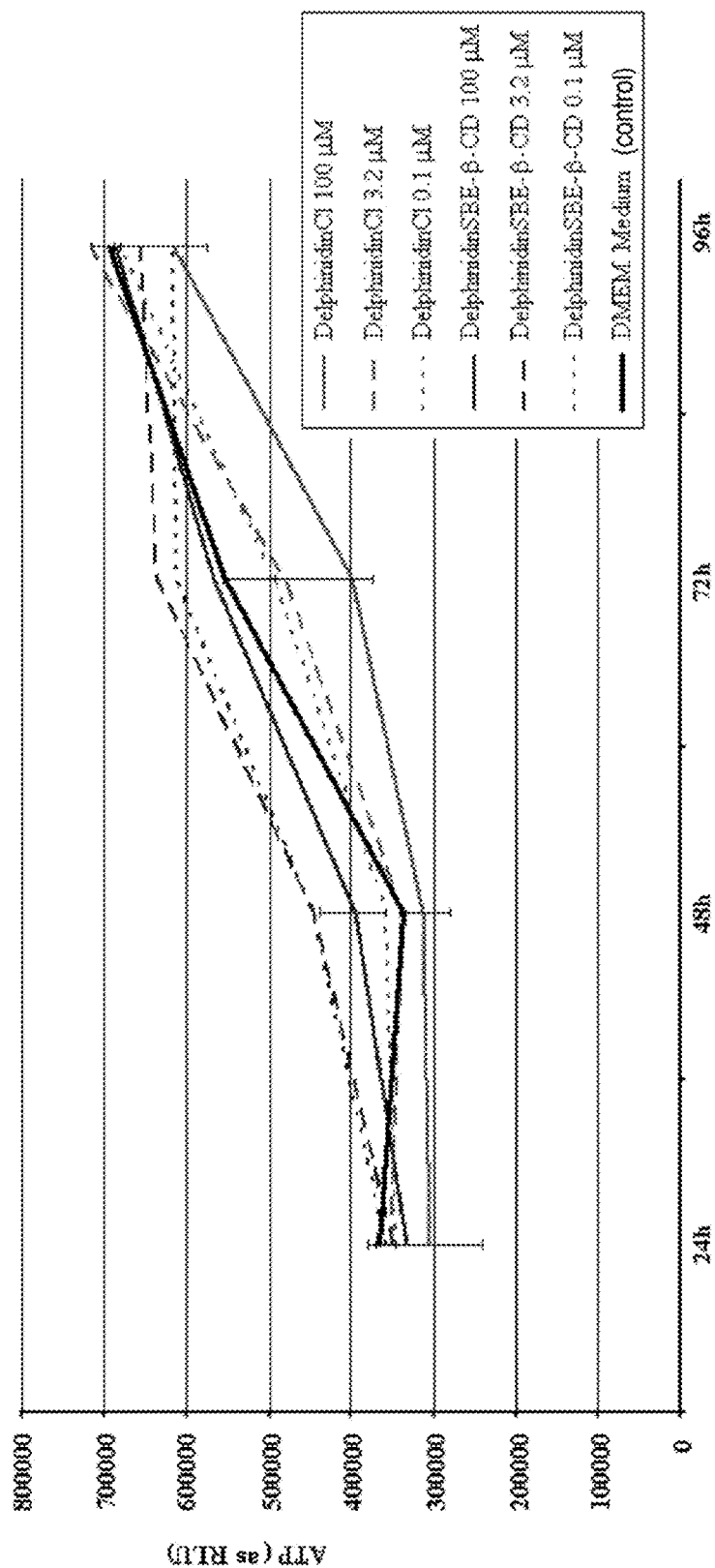
FIG. 18 shows the effect of delphinidin Cl and the delphinidin-SBE-β-CD complex at concentrations of 0.1 µM, 3.2 µM and 100 µM compared to active ingredient-free control medium on the vitality of endothelial cells using the ATP luminescence assay.

The experimental results of the ATP luminescence assay are presented graphically in FIGS. 18 (endothelial cells) and 19 (fibroblasts) and can be summarized as follows:

delphinidin Cl and delphinidin-SBE-β-CD show no significant cytotoxic effects on human fibroblasts and endothelial cells at the active ingredient concentration investigated (0.1-100 µM).

This opens up a completely new and particularly suitable active ingredient group for treating cancer, the active ingredients delphinidin Cl and delphinidin-SBE-β-CD investigated having on the one hand the desired antiproliferative effects on cancer cells (melanoma cells) (Examples 6-11) while on the other hand avoiding the generally expected undesired cytotoxic (side) effects on non-cancerous cells at therapeutic active ingredient concentrations according to the present Example 12.

The invention claimed is:

1. A composition comprising:
   a complex of delphinidin and a sulfoalkyl ether β-cyclodextrin for use in the treatment of malignant melanoma.

2. The composition of claim 1, characterized in that the sulfoalkyl ether β-cyclodextrin in the complex is a sulfobutyl ether β-cyclodextrin.

3. The composition of claim 1, characterized in that the composition comprises a therapeutically active amount of the complex of delphinidin and sulfoalkyl ether β-cyclodextrin.

4. The composition of claim 1, characterized in that the composition is used as a mono-preparation.

5. The composition of claim 1, characterized in that the composition comprises at least one further therapeutically active substance.

6. The composition of claim 5, characterized in that the therapeutically active substance is selected from the group consisting of
   cytostatics,
   interferons, and
   tumor vaccines.

7. The composition of claim 5, wherein said interferons comprise alpha- and/or beta-interferons.

8. The composition of claim 5, wherein said interferons comprise interferon alpha-2a and/or alpha-2b.

9. The composition of claim 1, wherein the degree of substitution of the cyclodextrin with sulfoalkyl ether groups in the complex is 3 to 8.

10. The composition of claim 1, wherein the degree of substitution of the cyclodextrin with sulfoalkyl ether groups in the complex is 4 to 8.

11. The composition of claim 1, wherein the degree of substitution of the cyclodextrin with sulfoalkyl ether groups in the complex is 5 to 8.

12. The composition of claim 1, wherein the degree of substitution of the cyclodextrin with sulfoalkyl ether groups in the complex is 6 to 7.

13. The composition of claim 1, further comprising one or more pharmaceutical auxiliaries and/or additives.

14. The composition of claim 13, wherein said one or more pharmaceutical auxiliaries and/or additives are selected from the group consisting of a pharmaceutically acceptable carrier, fillers, odorants and stabilizers.

15. The composition of claim 1, wherein said composition is formulated for administration in a form selected from the group consisting of oral, rectal, parenteral, including intraperitoneal, percutaneous, subcutaneous, intramuscular, intravenous, ophthalmic, pulmonary and nasal.

16. The composition for use as claimed in claim 15, characterized in that the administration form is selected from the group consisting of tablet, capsule, suspension, aerosol, solution, cream, paste, lotion, gel and salve.

17. The composition of claim 1, characterized in that the complex of delphinidin and the sulfoalkyl ether β-cyclodextrin are used in a galenic preparation for controlled and/or delayed release of the delphinidin.

18. A method of treating malignant melanoma in a subject, comprising administering a composition of claim 1 to said subject.

19. A method of treating malignant melanoma in a subject who has been subjected to, is being subjected to, or is being prepared for a treatment selected from the group consisting of surgical removal of melanoma cells or tissues affected with malignant melanoma,
radiotherapy,
immunotherapy,
chemotherapy and
interferon treatment,
comprising administering the composition of claim 1 to said subject.

\* \* \* \* \*